United States Patent [19]
Yoon et al.

[11] Patent Number: 6,004,332
[45] Date of Patent: Dec. 21, 1999

[54] SUTURING INSTRUMENT WITH MULTIPLE ROTATABLY MOUNTED OFFSET NEEDLE HOLDERS AND METHOD OF USING THE SAME

[76] Inventors: InBae Yoon, 2101 Highland Ridge Dr., Phoenix, Md. 21131; Samuel C. Yoon, 719 Leister Dr., Timonium, Md. 21093

[21] Appl. No.: 08/847,254

[22] Filed: May 1, 1997

[51] Int. Cl.⁶ .................................................. A61B 17/04
[52] U.S. Cl. ......................... 606/144; 606/139; 606/148
[58] Field of Search .................................. 606/144, 148, 606/139, 205, 206, 207

[56] References Cited

U.S. PATENT DOCUMENTS

| | | |
|---|---|---|
| 919,138 | 4/1909 | Drake et al. . |
| 1,037,864 | 9/1912 | Carlson et al. . |
| 1,131,163 | 3/1915 | Saunders et al. . |
| 1,155,378 | 10/1915 | Steedman . |
| 1,449,087 | 3/1923 | Bugbee . |
| 1,822,330 | 9/1931 | Ainslie . |
| 1,916,722 | 7/1933 | Ende . |
| 2,213,830 | 9/1940 | Anastasi . |
| 2,580,964 | 1/1952 | Skaller . |
| 2,601,564 | 6/1952 | Smith . |
| 2,646,045 | 7/1953 | Priestley . |
| 2,959,172 | 11/1960 | Held . |
| 3,090,386 | 5/1963 | Curtis . |
| 3,139,089 | 6/1964 | Scherwin . |
| 3,349,772 | 10/1967 | Rygg . |
| 3,470,875 | 10/1969 | Johnson . |
| 3,842,840 | 10/1974 | Schweizer . |
| 3,946,740 | 3/1976 | Bassett . |
| 4,109,658 | 8/1978 | Hughes . |
| 4,164,225 | 8/1979 | Johnson et al. . |
| 4,257,420 | 3/1981 | Terayama . |
| 4,440,171 | 4/1984 | Nomoto et al. . |
| 4,557,265 | 12/1985 | Andersson . |
| 4,621,640 | 11/1986 | Mulhollan et al. . |
| 4,635,638 | 1/1987 | Weintraub et al. . |
| 4,935,027 | 6/1990 | Yoon . |
| 5,037,433 | 8/1991 | Wilk et al. . |
| 5,100,421 | 3/1992 | Christoudias . |
| 5,147,373 | 9/1992 | Ferzli ..................................... 606/144 |
| 5,152,769 | 10/1992 | Baber . |
| 5,171,257 | 12/1992 | Ferzli ..................................... 606/205 |
| 5,181,919 | 1/1993 | Bergman et al. . |
| 5,209,741 | 5/1993 | Spaeth . |
| 5,211,650 | 5/1993 | Noda . |
| 5,222,508 | 6/1993 | Contarini . |
| 5,224,948 | 7/1993 | Abe et al. . |
| 5,234,443 | 8/1993 | Phan et al. . |
| 5,244,948 | 9/1993 | Mulhaupt et al. . |
| 5,261,917 | 11/1993 | Hasson et al. . |
| 5,281,238 | 1/1994 | Chin et al. . |
| 5,300,082 | 4/1994 | Sharpe et al. . |
| 5,304,185 | 4/1994 | Taylor . |
| 5,305,121 | 4/1994 | Moll . |
| 5,308,353 | 5/1994 | Beurrier . |
| 5,320,632 | 6/1994 | Heidmueller . |
| 5,336,230 | 8/1994 | Leichtling et al. ..................... 606/148 |
| 5,336,231 | 8/1994 | Adair . |

(List continued on next page.)

FOREIGN PATENT DOCUMENTS

| | | |
|---|---|---|
| 0482881A1 | 4/1992 | European Pat. Off. . |
| 0337579 | 4/1904 | France . |
| 0395073 | 8/1973 | U.S.S.R. . |
| 2260704 | 4/1993 | United Kingdom . |
| WO 97/37583 | 10/1997 | WIPO . |

*Primary Examiner*—Glenn K. Dawson
*Assistant Examiner*—Tina T. D. Pham
*Attorney, Agent, or Firm*—Blank Rome Comisky & McCauley LLP

[57] ABSTRACT

An instrument for suturing anatomical tissue with a suture needle includes a barrel having two needle holding apparatus therein which can be manipulated from a proximal end of the barrel. Jaws of each needle holding apparatus are offset from a rotatable shaft by a transverse arm. In an insertion position, the jaws are confined within the diametrical dimension of the barrel at a distal end thereof. After insertion, the jaws can be manipulated to extend beyond the diametrical dimension of the barrel to provide a large working span in which tissue can be sutured.

52 Claims, 13 Drawing Sheets

U.S. PATENT DOCUMENTS

| | | |
|---|---|---|
| 5,356,424 | 10/1994 | Buzerak et al. . |
| 5,364,408 | 11/1994 | Gordon . |
| 5,364,409 | 11/1994 | Kuwabara et al. . |
| 5,374,275 | 12/1994 | Bradley et al. . |
| 5,376,096 | 12/1994 | Foster . |
| 5,389,098 | 2/1995 | Tsuruta et al. . |
| 5,389,103 | 2/1995 | Melzer et al. . |
| 5,395,367 | 3/1995 | Wilk . |
| 5,397,325 | 3/1995 | Della Badia et al. . |
| 5,403,328 | 4/1995 | Shallman . |
| 5,403,329 | 4/1995 | Hinchcliffe . |
| 5,437,681 | 8/1995 | Meade et al. . |
| 5,454,823 | 10/1995 | Richardson et al. . |
| 5,462,561 | 10/1995 | Voda . |
| 5,462,562 | 10/1995 | Elkus . |
| 5,468,251 | 11/1995 | Buelna . |
| 5,470,338 | 11/1995 | Whitfield et al. . |
| 5,474,057 | 12/1995 | Makower et al. . |
| 5,474,568 | 12/1995 | Scott . |
| 5,477,794 | 12/1995 | Klundt . |
| 5,478,344 | 12/1995 | Stone et al. . |
| 5,478,345 | 12/1995 | Stone et al. . |
| 5,480,406 | 1/1996 | Nolan et al. . |
| 5,496,310 | 3/1996 | Exconde et al. . |
| 5,496,334 | 3/1996 | Klundt et al. . |
| 5,503,634 | 4/1996 | Christy . |
| 5,520,703 | 5/1996 | Essig et al. . |
| 5,540,704 | 7/1996 | Gordon et al. . |
| 5,540,705 | 7/1996 | Meade et al. . |
| 5,545,148 | 8/1996 | Wurster . |
| 5,562,640 | 10/1996 | McCabe et al. . |
| 5,562,685 | 10/1996 | Mollenauer et al. . |
| 5,562,686 | 10/1996 | Sauer et al. . |
| 5,562,703 | 10/1996 | Desai . |
| 5,569,164 | 10/1996 | Lurz . |
| 5,569,269 | 10/1996 | Hart et al. . |
| 5,569,270 | 10/1996 | Weng . |
| 5,573,542 | 11/1996 | Stevens . |
| 5,578,048 | 11/1996 | Pasqualucci et al. . |
| 5,582,617 | 12/1996 | Klieman et al. . |
| 5,591,181 | 1/1997 | Stone et al. . |
| 5,601,575 | 2/1997 | Measamer et al. . |
| 5,603,718 | 2/1997 | Xu . |
| 5,607,435 | 3/1997 | Sachdeva et al. . |
| 5,609,601 | 3/1997 | Kolesa et al. . |
| 5,626,588 | 5/1997 | Sauer et al. . |
| 5,632,751 | 5/1997 | Piraka . |
| 5,632,752 | 5/1997 | Buelna . |
| 5,637,112 | 6/1997 | Moore et al. ............................ 606/148 |
| 5,643,292 | 7/1997 | Hart . |
| 5,662,663 | 9/1997 | Shallman . |
| 5,665,096 | 9/1997 | Yoon ........................................ 606/139 |
| 5,668,525 | 9/1997 | Ishibashi et al. ........................ 606/206 |
| 5,674,230 | 10/1997 | Tovey et al. . |
| 5,683,349 | 11/1997 | Makover et al. ........................ 606/214 |
| 5,702,407 | 12/1997 | Kaji ........................................ 606/139 |
| 5,707,379 | 1/1998 | Fleenor et al. . |
| 5,709,693 | 1/1998 | Taylor . |
| 5,709,694 | 1/1998 | Greenberg et al. . |
| 5,713,908 | 2/1998 | Jameel et al. . |
| 5,722,990 | 3/1998 | Sugarbaker et al. . |
| 5,810,805 | 9/1998 | Sutcu et al. . |
| 5,810,852 | 9/1998 | Greenberg et al. .................... 606/148 |

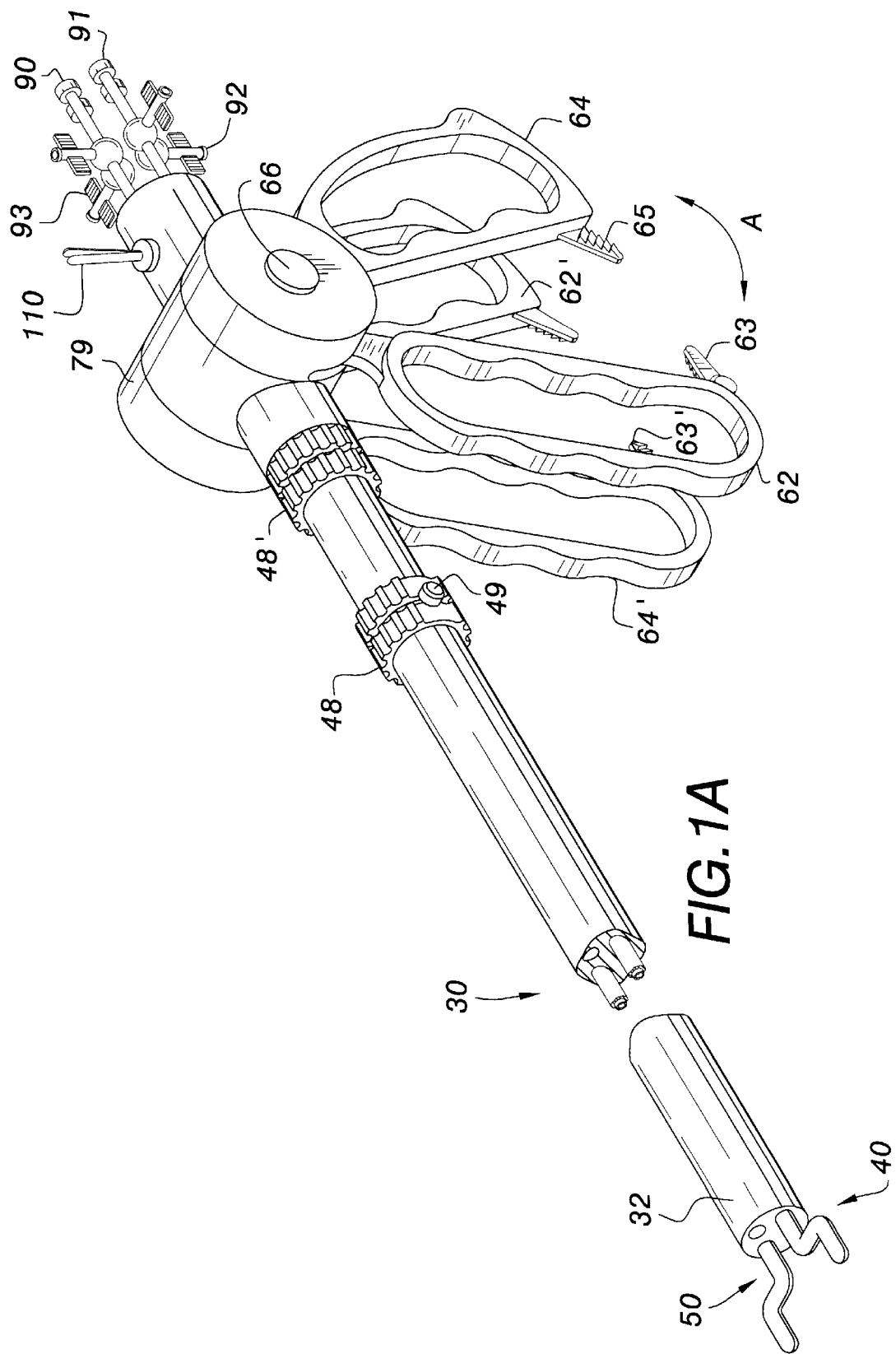

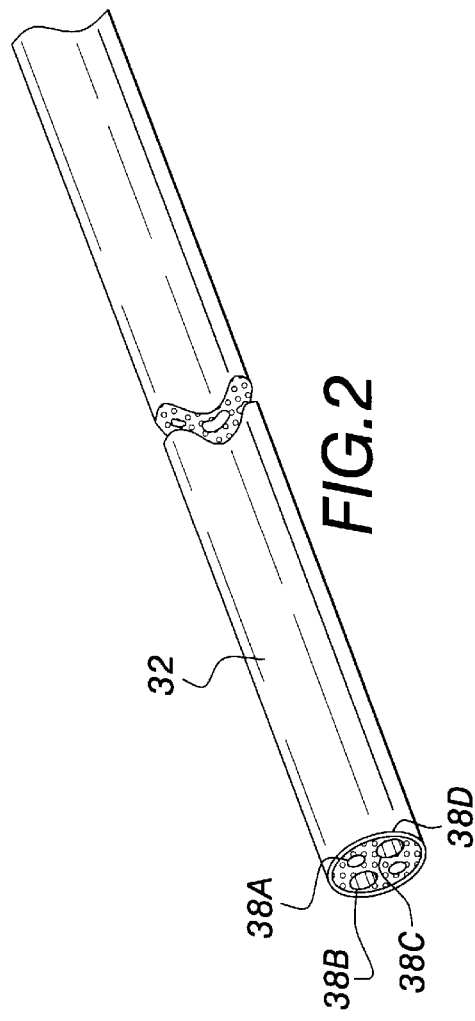
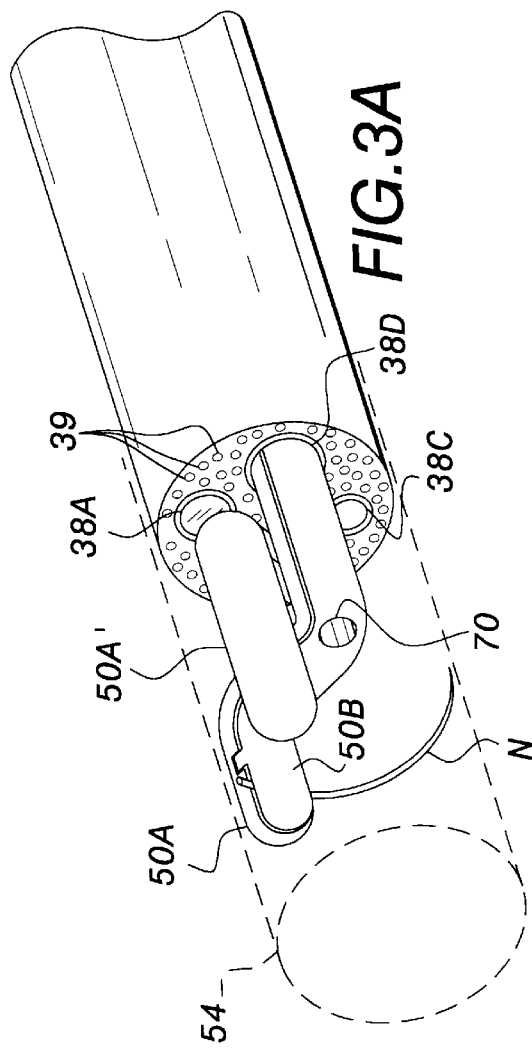
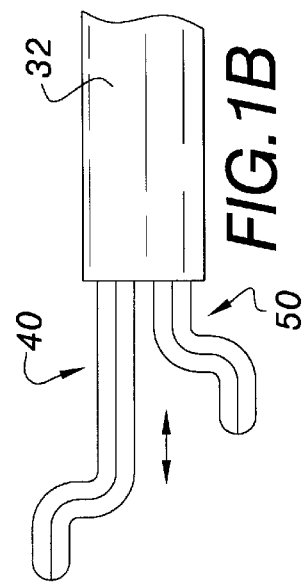
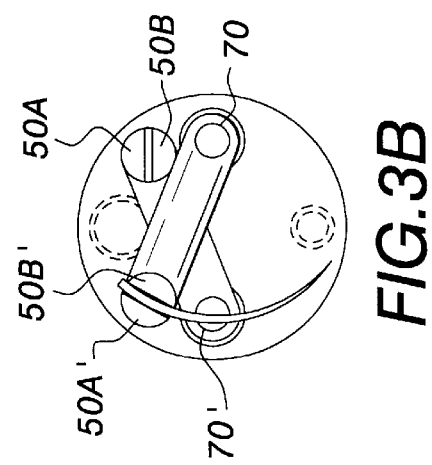

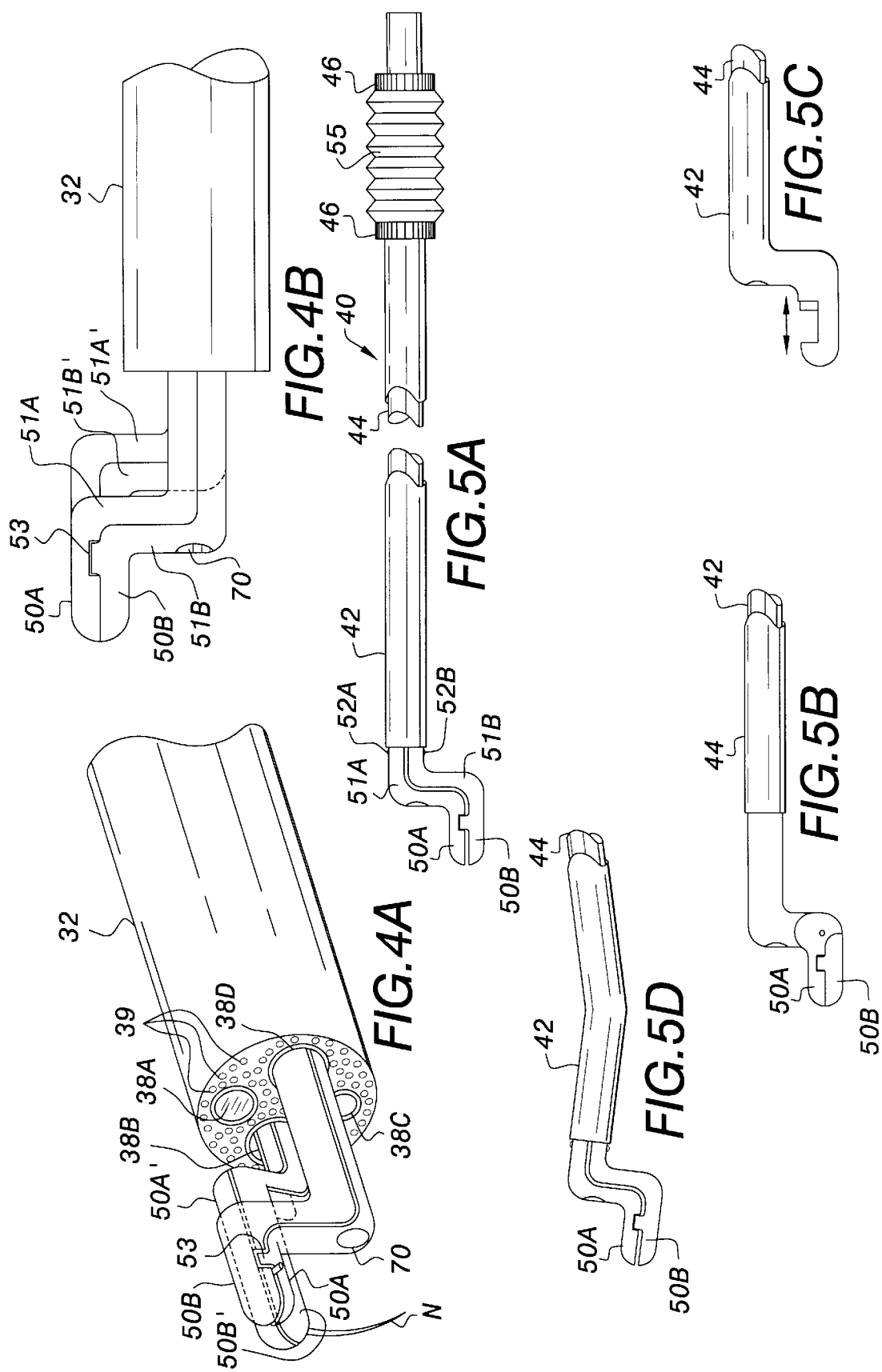

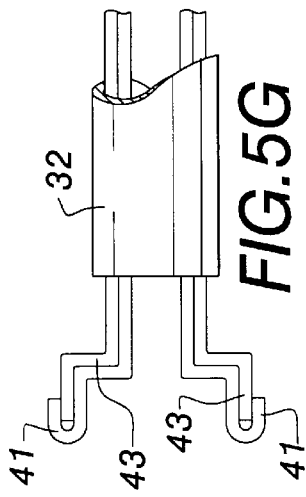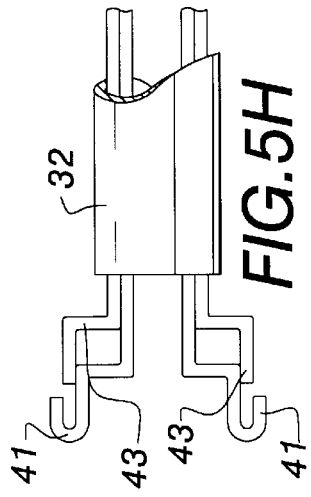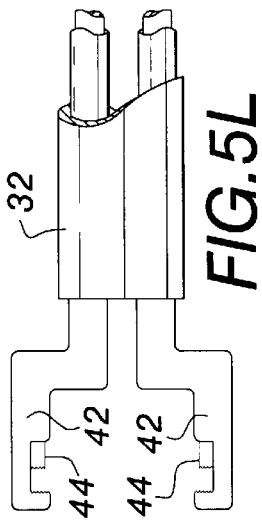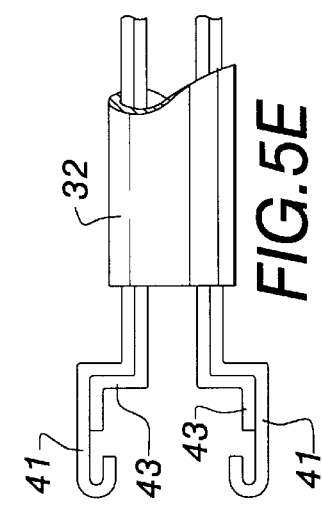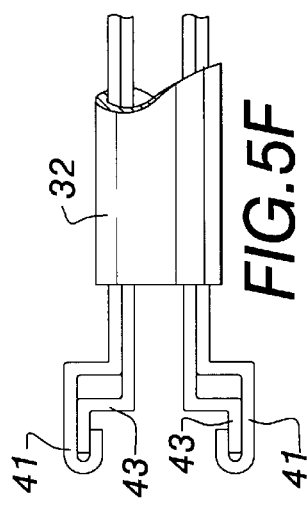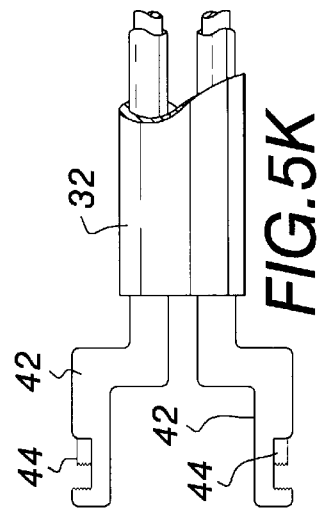

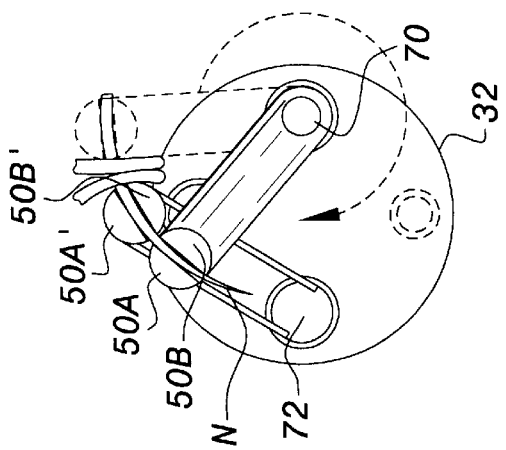
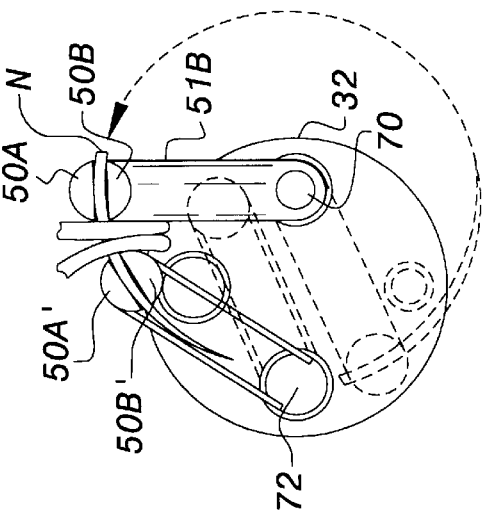
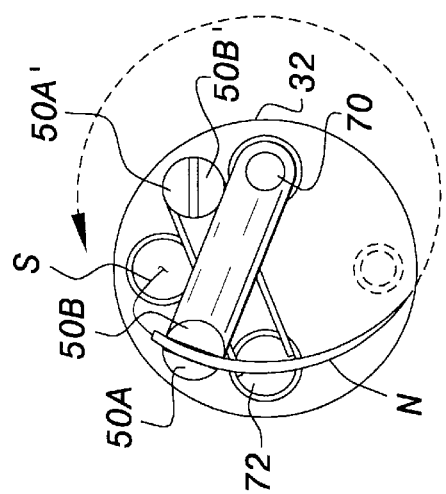

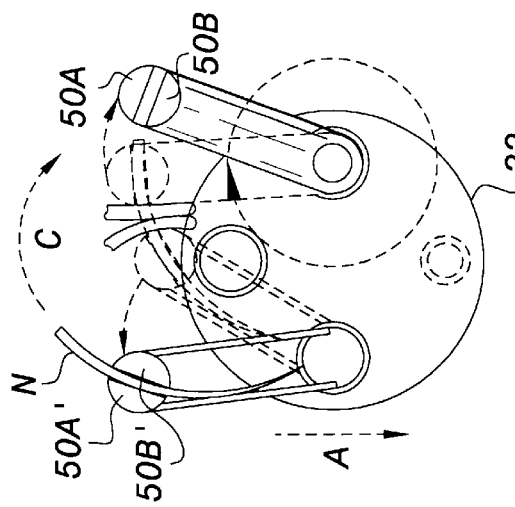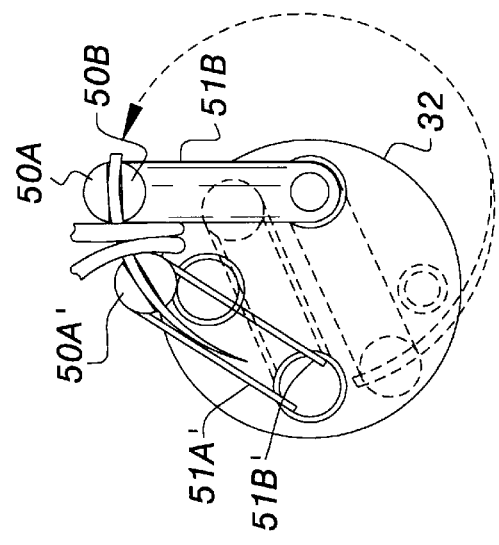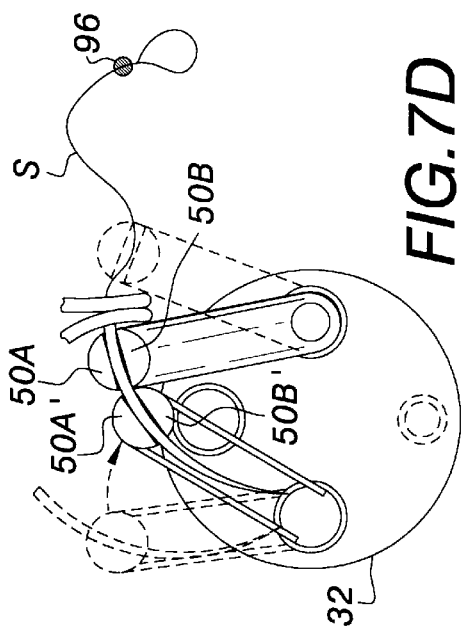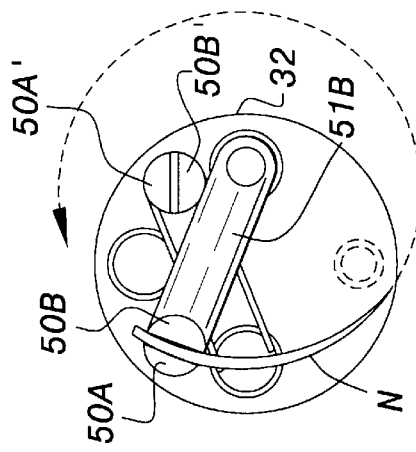

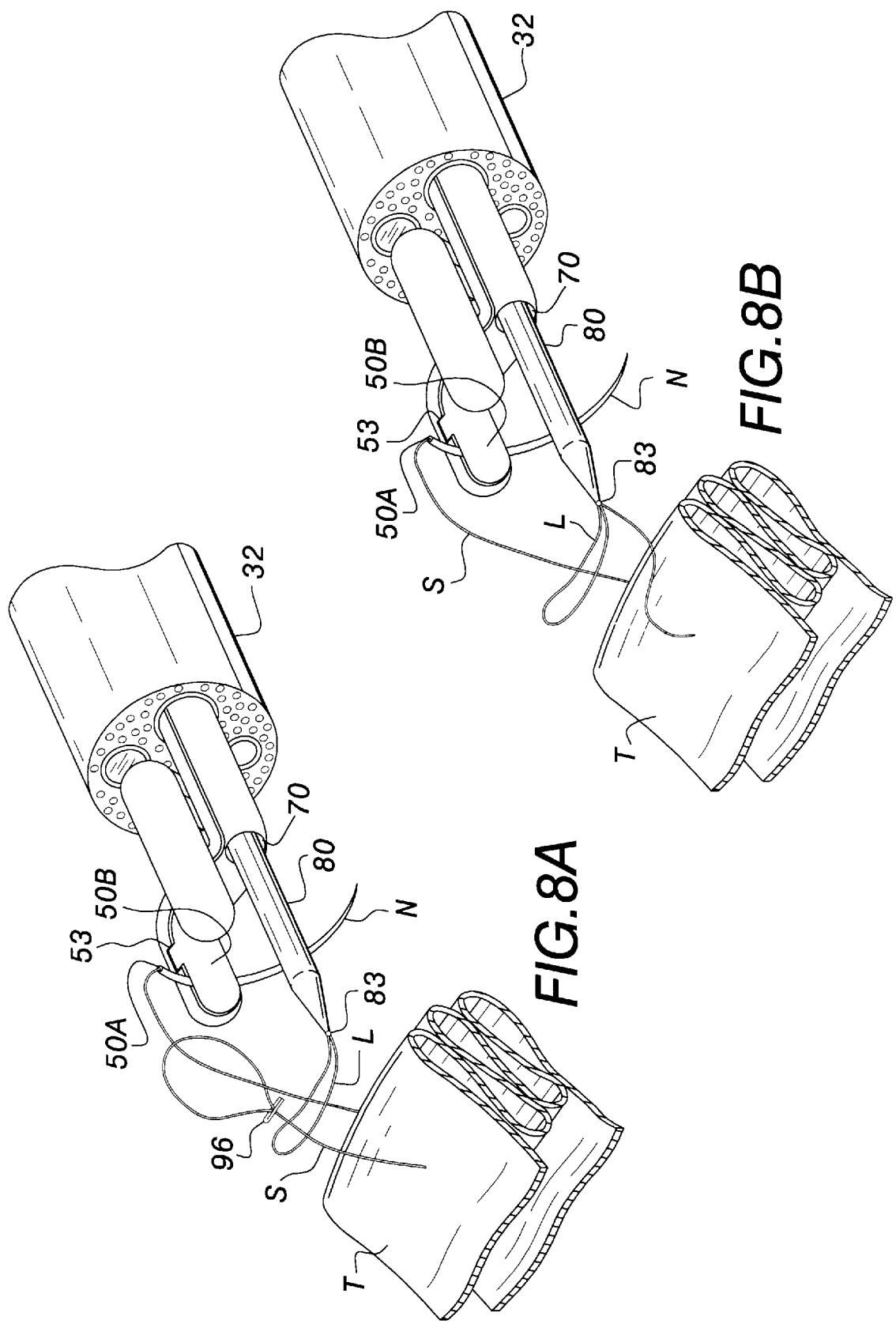

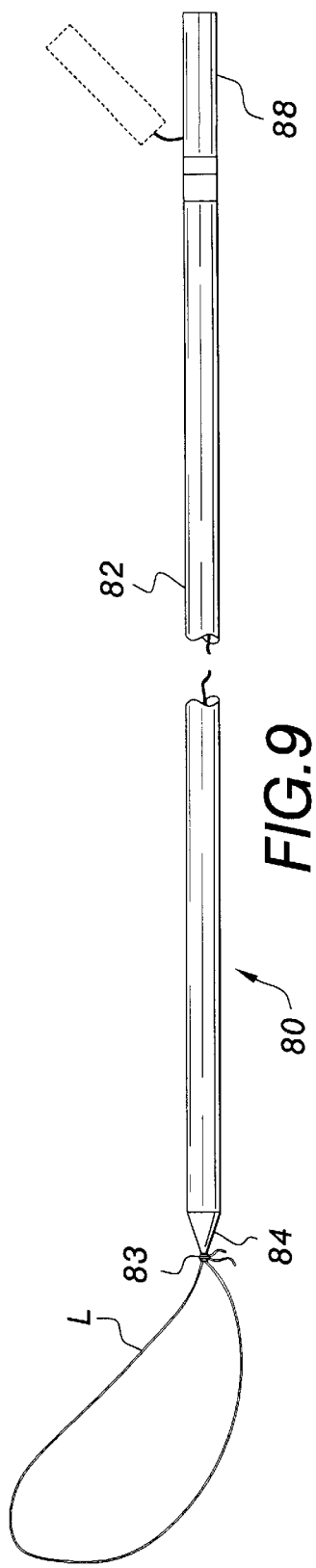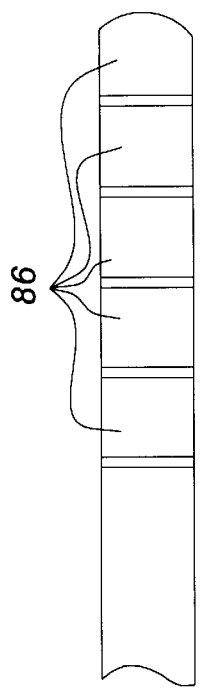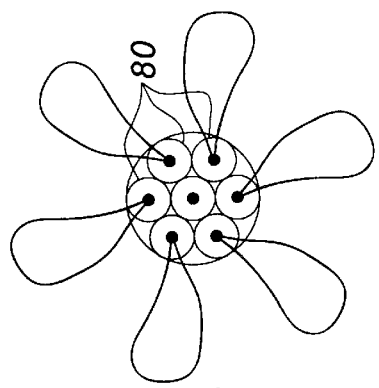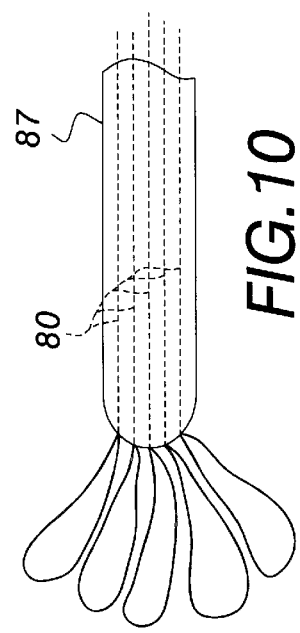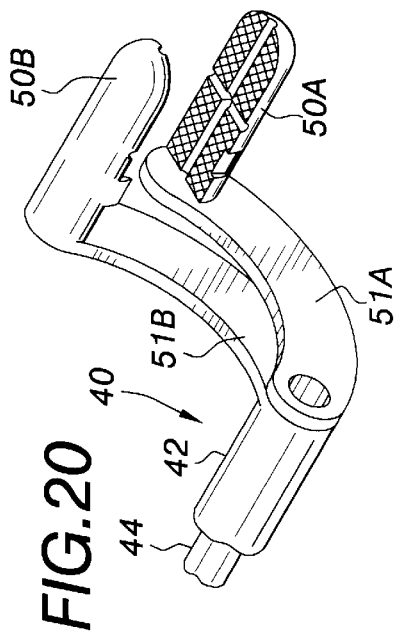
FIG. 9
FIG. 10
FIG. 11
FIG. 20

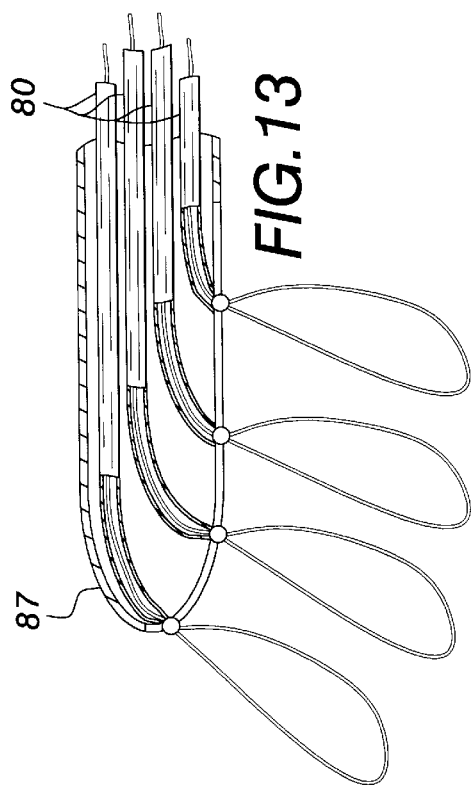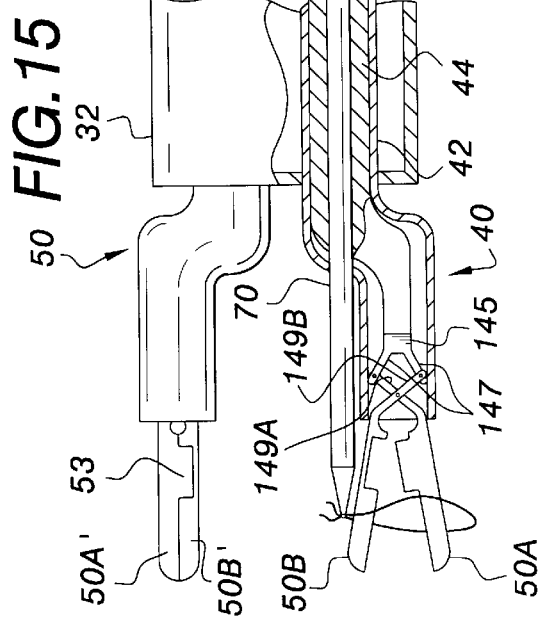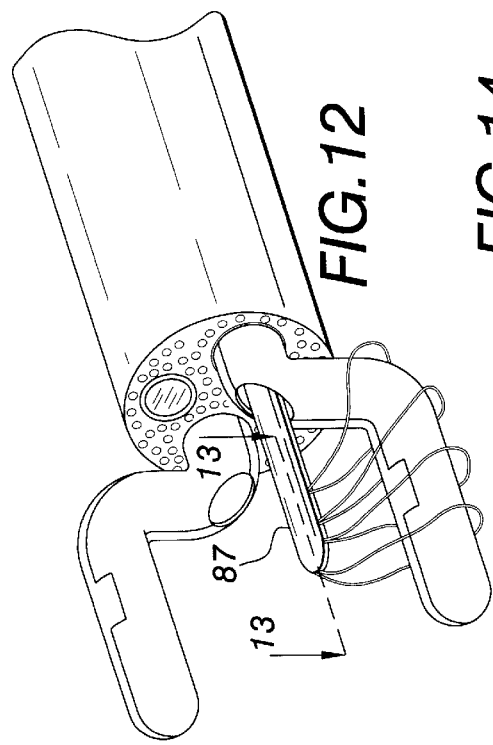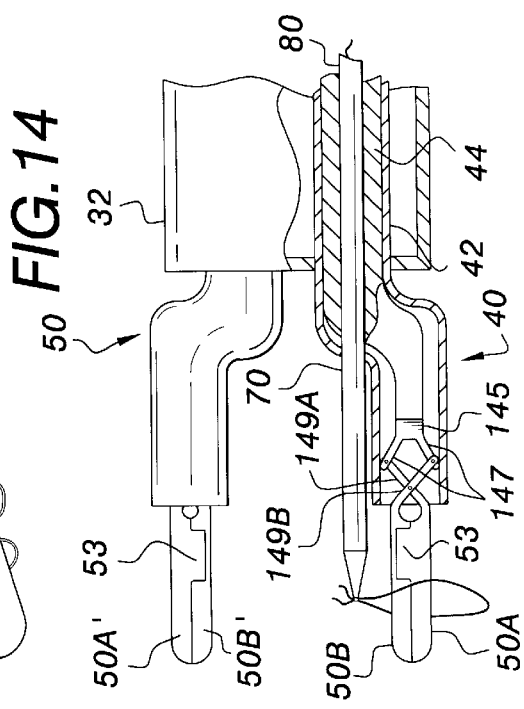

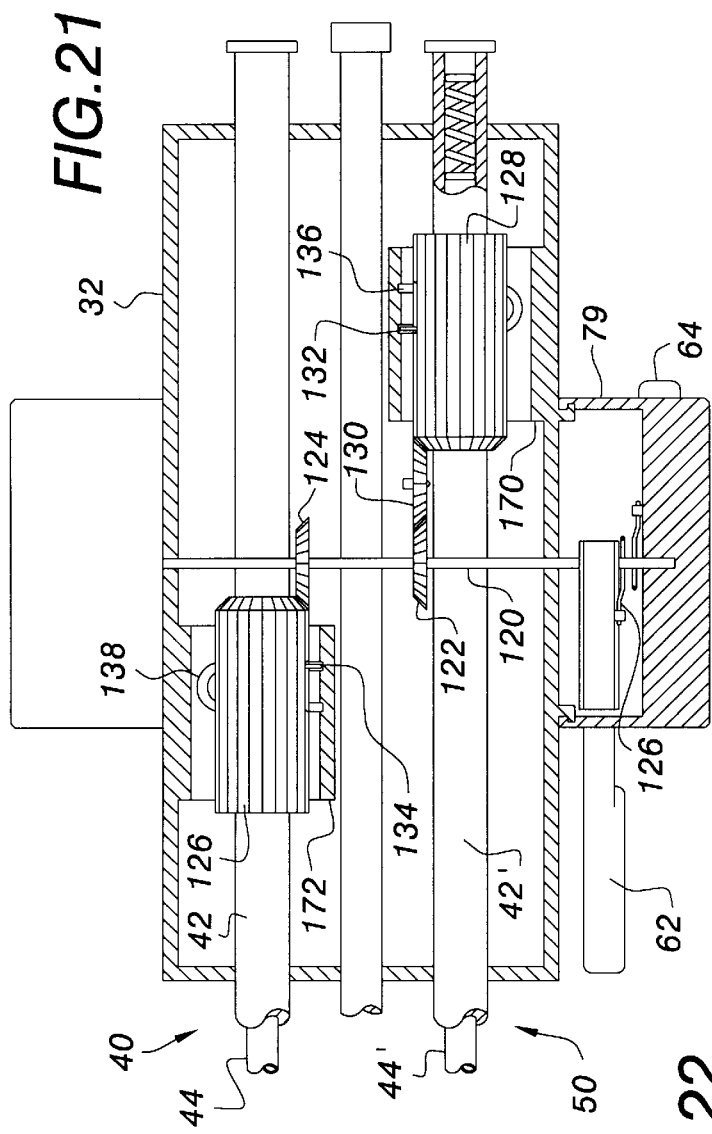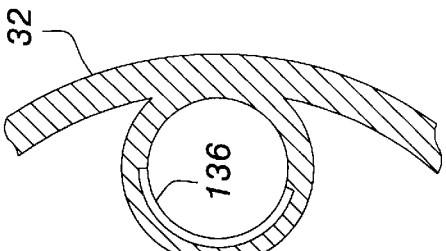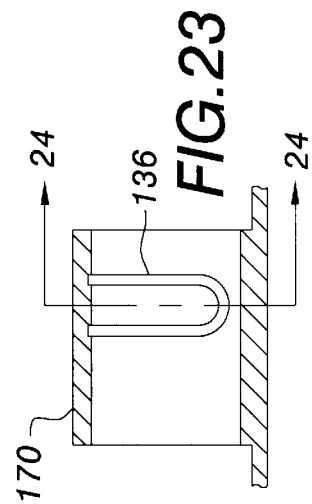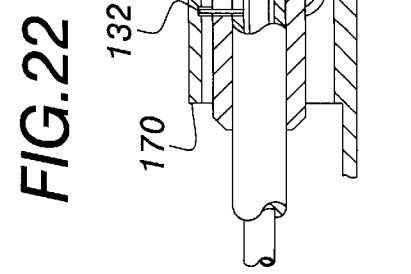

ID NO. 6,004,332

SUTURING INSTRUMENT WITH MULTIPLE ROTATABLY MOUNTED OFFSET NEEDLE HOLDERS AND METHOD OF USING THE SAME

RELATED PATENT APPLICATION DATA

This application is related to applicant's copending applications Ser. No. 08/366,285 filed on Dec. 29, 1994, Ser. No. 08/377,723 filed on Jan. 25, 1995, Ser. No. 08/401,002 filed Mar. 9, 1995, Ser. No. 08/585,875 filed Jan. 16, 1996, and Ser. No. 08/758,648 filed Nov. 27, 1996, the disclosures of which are incorporated herein by reference. Also, this application is related to applicant's concurrently filed applications entitled "Surgical Instrument with Rotatably Mounted Offset End Effector and Method of Using the Same", "Suturing Instrument with Rotatably Mounted Offset Needle Holder and Method of Using the Same", and "Surgical Instrument with Multiple Rotatably Mounted Offset End Effectors and Method of Using the Same", the disclosures of which are also incorporated herein by reference.

BACKGROUND OF THE INVENTION

1. Field of the Invention

The present invention pertains to suturing of bodily or anatomical tissue and, more particularly, to an apparatus and method for suturing anatomical tissue during endoscopic and open surgical procedures.

2. Discussion of the Related Art

Suturing of bodily tissue, that is, the practice of using lengths of suture material to ligate or approximate tissue, is a time consuming part of most surgical procedures including both open surgery and endoscopic or closed surgery. "Open surgery" refers to surgery wherein the surgeon gains access to the surgical site by a relatively large incision and "endoscopic surgery" refers to minimally invasive surgery wherein the surgeon gains access to the surgical site via one or more portals through which endoscopes are introduced to view the surgical site and through which instruments, such as forceps, cutters, needle holders and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue, the surgeon ties a knot in the suture material. The knotting procedure allows the surgeon to adjust the tension on the suture material to accommodate the particular tissue being sutured and to control approximation, occlusion, attachment or other conditions of the tissue.

The process of tissue penetration and knotting of the suture material can be time consuming and tedious work, particularly when performed in connection with microsurgery and endoscopic surgery and can unduly prolong the duration of surgery and therefore the period in which the patient is under anesthesia. Nevertheless, endoscopic surgery is preferred over open surgery due to the greatly reduced trauma and wound healing time for the patient and due to cost savings associated with shorter hospital stays and performing surgery in non-hospital or outpatient surgery sites. Accordingly, there has been much effort to develop techniques for facilitating the suturing normally performed by use of a suture needle and a length of suture material. Alternative techniques proposed have included electrical coagulation, mechanical devices such as clips, clamps and staples, and lasers. However, no alternative technique has yet been well accepted by surgeons to produce the results obtained by suturing and knotting. Thus, there is a great need for suturing techniques useful in endoscopic surgery to permit surgeons to suture anatomical tissue using suture needles and lengths of suture material in a time efficient, consistent and precise manner.

The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, scissors, forceps, needle holders and the like (known generally as "end effectors") into the anatomical cavity.

Suturing is typically performed with a needle holding instrument, or needle holder, having a pair of jaws adapted to hold the body of a suture needle. The jaws of the needle holding instrument are inserted through the portal sleeve and are positioned at the operative site by manipulation of a handle at the proximal end of the instrument outside the body. With a suture needle held between the jaws of the needle holding instrument, the handle is manipulated to cause a tip of the needle to be pushed through the tissue being sutured. Once the tip of the suture needle has been pushed through the tissue, the jaws of the needle holding instrument must be opened to release the suture needle so that the tip of the needle can be grasped and pulled through the tissue therewith, or, after opening the jaws, a second needle holding instrument must be introduced at the operative site through another portal to grasp the tip of the suture needle after it has emerged from the tissue being sutured.

The former technique requires difficult manipulation and further adjustment of the suture needle within the jaws of the needle holder before another stitch can be made. While use of a second needle holding instrument for pulling the needle through the anatomical tissue allows the first needle holding instrument to grasp the body of the suture needle in the manner required to make additional stitches, a second puncture site is required to permit insertion of the second instrument. It is generally desirable to minimize the number of puncture sites created for performing a particular endoscopic procedure.

Of course, it is also generally desirable to minimize the size of each puncture site. Further, in order to permit a wide range of tissue size to be sutured, it is desirable to provide a wide range of relative movement between the two needle holder instruments, i.e. a large working span. These objectives, minimal number punctures, small size of punctures, and a wide range of relative movement, are seemingly contradictory. Conventional devices have not achieved the above-noted objectives in a satisfactory manner.

SUMMARY OF THE INVENTION

Accordingly, it is a primary object of the present invention to overcome the above-mentioned disadvantages of the prior art and to improve suturing instruments and methods of suturing anatomical tissue.

Yet another object of the present invention is to minimize the number of puncture sites required for suturing anatomical tissue in an endoscopic procedure by inserting a pair of needle holders and other instruments through a single puncture site with a suturing instrument that is operable to move the needle holders relative to one another in a cooperative manner to suture anatomical tissue.

It is a further object of the present invention to permit a suturing instrument as well as other medical instruments and devices to be introduced through a single portal in an endoscopic procedure without having to withdraw the suturing instrument from the portal.

It is another object of the invention to permit an endoscopic suturing device to have a large working span and a small insertion diameter and to replicate the natural motion of needle passage through tissue.

Finally, it is an object of the invention to control an endoscopic or open surgical suturing procedure with standard proximal end controls.

The present invention allows suturing of anatomical tissue to be accomplished in a time efficient, consistent and precise manner. Also, suturing can be accomplished using standard suture needles and filamentous suture materials without the need for additional instruments at the operative site.

A first aspect of the present invention is generally characterized in an instrument for suturing anatomical tissue with a suture needle including a barrel, a needle driver having a shaft that is mounted in the barrel for rotation about a first axis, and a needle catcher having a shaft that is mounted in the barrel for rotation about a second axis. The needle driver and the needle catcher each include needle holding jaw members offset from the first and second axes respectively and selectively operable to grasp and release the suture needle. The jaw members are coupled to the shafts by arms or connecting portions extending from a distal end of the shafts. When the jaw members of the needle driver are operated to grasp the suture needle., the needle driver can be rotated to drive the suture needle through anatomical tissue positioned between the needle driver and the needle catcher, and when the jaw members of the needle catcher are operated to grasp the suture needle, the jaw members of the needle driver can be operated to release the suture needle, thereby allowing the needle catcher to be rotated to pull the suture material through the anatomical tissue. During insertion into an anatomical cavity through a portal or the like, the jaw members are contained within a diametrical dimension of the instruments. However during suturing, the jaw members can extend beyond this dimension due to the offset configuration.

Another aspect of the present invention is generally characterized in a method of suturing anatomical tissue using a length of suture material attached to a suture needle. The method includes the steps of grasping the suture needle with offset jaw members of a needle driver, positioning the anatomical tissue between a tip of the suture needle and a needle catcher, rotating the needle driver in a first direction to cause the tip of the needle to penetrate the anatomical tissue, receiving the tip Of the suture needle in offset jaw members of the needle catcher, grasping the suture needle with the needle catcher, releasing the suture needle from the needle driver, and rotating the needle catcher to pull the needle and the suture material through the anatomical tissue.

In another aspect of the invention, a needle driver and a needle catcher having offset jaw members are used with a ligating instrument. The ligating instrument carries one or more loops of suture material that can be drawn tightly around a knotting element or the like to secure suture material after it has been passed through the tissue by the needle driver. The ligating instrument is inserted through an operating channel formed in the shaft of the needle driver or the needle catcher.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

FIG. 1A illustrates the suturing instrument of the first preferred embodiment;

FIG. 1B illustrates distal and proximal movement of the needle driver and needle catcher;

FIG. 2 is a perspective view of a portion of the barrel of the first preferred embodiment;

FIG. 3A is a perspective view of the distal end of the first preferred embodiment in the insertion position;

FIG. 3B is an end view of the distal end of the first preferred embodiment in the insertion position;

FIG. 4A is a perspective view of the distal end of the first preferred embodiment in an operating position;

FIG. 4B is a side view of the distal end of the first preferred embodiment in an operating position;

FIG. 5 is a side view of the needle driver of the first preferred embodiment removed from the barrel;

FIG. 5B illustrates the distal end of a modified driver;

FIG. 5C illustrates the distal end of another modified driver;

FIG. 5D illustrates the distal end of another modified driver;

FIG. 5E illustrates a distal end of the first preferred embodiment with modified jaws in the open position;

FIG. 5F illustrates a distal end of the first preferred embodiment with the modified jaws in the closed position;

FIG. 5G illustrates a distal end of the first preferred embodiment with another modified jaws in the closed position;

FIG. 5H illustrates a distal end of the first preferred embodiment with another modified jaws in the open position;

FIG. 5K illustrates a distal end of the first preferred embodiment with another modified jaws;

FIG. 5L illustrates a distal end of the first preferred embodiment with another modified jaws.

FIGS. 6A–C are end views of the distal end illustrating a method for suturing using the preferred embodiment;

FIGS. 7A–D are end views illustrating another suturing method using the first preferred embodiment;

FIG. 8A is a perspective view of a distal end of the first preferred embodiment with a ligator inserted through an operating channel;

FIG. 8B illustrates an alternative ligator arrangement;

FIG. 9 illustrates the ligator of FIG. 8 removed from this suturing device;

FIG. 10 illustrates a ligator cluster;

FIG. 11 is an end view of the ligator cluster of FIG. 10;

FIG. 12 is a perspective view of the distal end of the first preferred embodiment with an alternative ligator cluster;

FIG. 13 is a sectional view of the distal end of the alternative ligator cluster of FIG. 12 taken along line 13—13;

FIGS. 14 and 15 are cross-sectional views of an alternative jaw configuration;

FIG. 20 illustrates the distal end of another driver;

FIG. 21 illustrates a mechanism for automatic one-handed operation;

FIG. 22 illustrates a portion of FIG. 21 in detail;

FIG. 23 illustrates a cylindrical member and cam groove of FIG. 21; and

FIG. 24 is a sectional view of FIG. 23 taken along line 24—24.

DETAILED DESCRIPTION OF THE PREFERRED EMBODIMENTS

Figure 17:
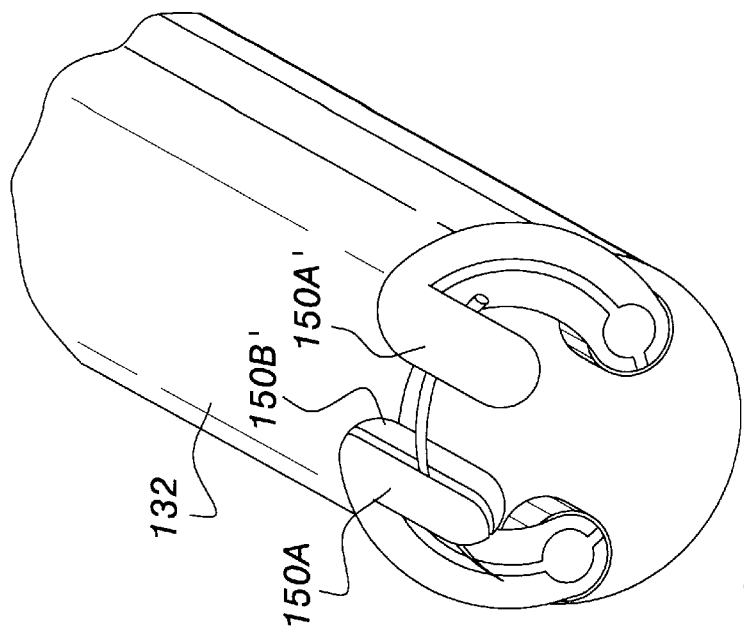
FIG. 17 is a perspective view of the second preferred embodiment in an operating position.

The suturing instrument of the present invention can be utilized to suture any type of anatomical tissue in any type of anatomical cavity. Accordingly, while the instrument is described hereinafter for use with a portal sleeve in endoscopic procedures, such as laparoscopy, the instrument can be used in open surgery and with catheters and other small and large diameter tubular or hollow cylindrical members providing access to small cavities, such as veins and arteries, as well as large cavities, such as the abdomen.

A suturing instrument according to a first preferred embodiment of the present invention is illustrated at 30 in FIG. 1A and includes cylindrical barrel, or outer shaft, 32 which has an elongated passage defined therein, needle driver 40, and needle catcher 50. Needle driver 40 and needle catcher 50 are substantially contained within cylindrical barrel 32 as is described in detail below. The terms "needle driver" and "needle catcher" are used herein to describe, in terms of their function, elements that may be structurally similar in the preferred embodiment. However, the function of these two elements herein is interchangeable. Also, these elements are sometimes referred to generically as "needle holders" herein. As shown in FIG. 1A, needle driver 40 and needle catcher 50 can be moved proximally and distally in barrel 32.

As shown in FIG. 2, barrel 32 has a plurality of channels 38a–d extending longitudinally there through. Barrel 32 can have additional channels for receiving one or more additional instruments to be introduced in the abdominal cavity or barrel 32 can have fewer channels as needed. Optical fibers 39 extend through barrel 32 to transmit light from a proximal light source to the body cavity of a patient. Channels 38a–d can be formed by thin wall, tubular sleeves extending longitudinally through barrel 32 or merely by void spaces defined by optical fibers 39.

FIG. 5. illustrates needle driver 40 removed from barrel 32 for illustrative purposes. Needle driver 40 includes elongated, tubular outer member 42 and elongated tubular inner member 44 disposed within outer member 42. Outer member 42 and inner member 44 define a shaft that is rotatable in barrel 32. Outer member 42 has a proximal end on which two diametrically enlarged flanges 46 are disposed. Flanges 46 serve to fix collar 55 on outer member 42 while permitting collar 55 to rotate with respect to outer member 42. The function of collar 55 is described in detail below.

Arms 51A and 51B serve as connecting members between jaw members 50A and 50B and inner member 44 and can be made entirely or partly of resilient, flexible or spring materials, or materials having shape memory. Jaw members 50A and 50B are biased to be normally disposed to an open position wherein the jaw members have a gap defined therebetween. This permits the shank of a suture needle to be placed between jaw members 50A and 50B and to be grasped thereby. Of course, the inner surfaces of jaw members 50A and 50B can be shaped to correspond to the needle shank, or any other appropriate way, to firmly grasp the needle when the jaw members 50A and 50B are in a closed position as shown in FIGS. 3A, 3B, 4A and 4B. Cam surfaces 52A and 52B are formed on arms 51A and 51B respectively. Needle driver 40 can be designed in various known ways permitting jaw members 50A and 50B to be movable between the closed position and the open position. The opening and closing movement of jaw members 50A and 50B in the first preferred embodiment is described below.

FIG. 5B illustrates an alternative needle driver 40 having jaw members 50A and 50B that pivot about a pin or the like. FIG. 5C illustrates an alternative needle driver 40 in which inner member 44 is resiliently flexible and outer member 42 has a notch formed therein. Movement of inner member 44 in the distal direction serves to grasp a needle or other object placed in the notch. FIG. 5D illustrates another modified needle driver 40 that is resiliently flexible and can be drawn proximally into barrel 32 to be straightened out and contained within the diametrical dimensions of barrel 32. In a free state, needle driver 40 of FIG. 5D is angled as shown. Of course each of these configurations can be applied to a needle catcher also.

FIG. 5E illustrates a distal end of instrument 30 having needle holders that include hooked member 41 and sliding keeper 43 that can be moved distally and proximally with respect to hook member 41. A needle can be grasped when keeper 43 is advanced distally to the closed position illustrated in FIG. 5F. FIG. 5G illustrates a similar arrangement. However, hook member 41 opens outwardly. FIG. 5H shows the open position with keeper 43 withdrawn. FIG. 5K illustrates a distal end of instrument 30 having needle driver holders that are configured as illustrated in FIG. 5C. FIG. 5L illustrates a similar configuration. However, in FIG. 5L, the notch in outer member 42 opens outwardly.

Figure 18:
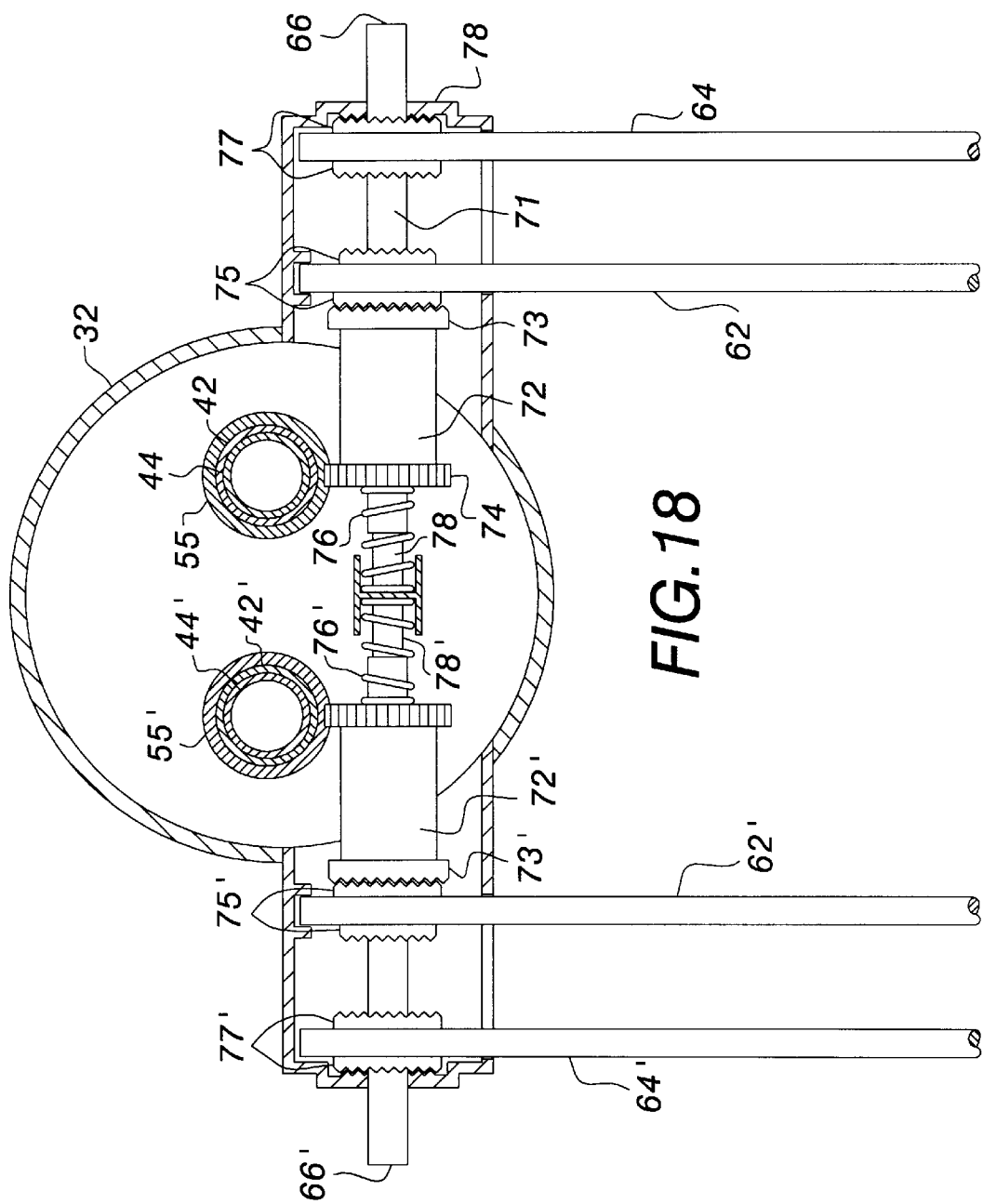
FIG. 18 is a sectional view of the proximal controls or the first preferred embodiment taken along lien 18—18 of FIG. 1.
Figure 19:
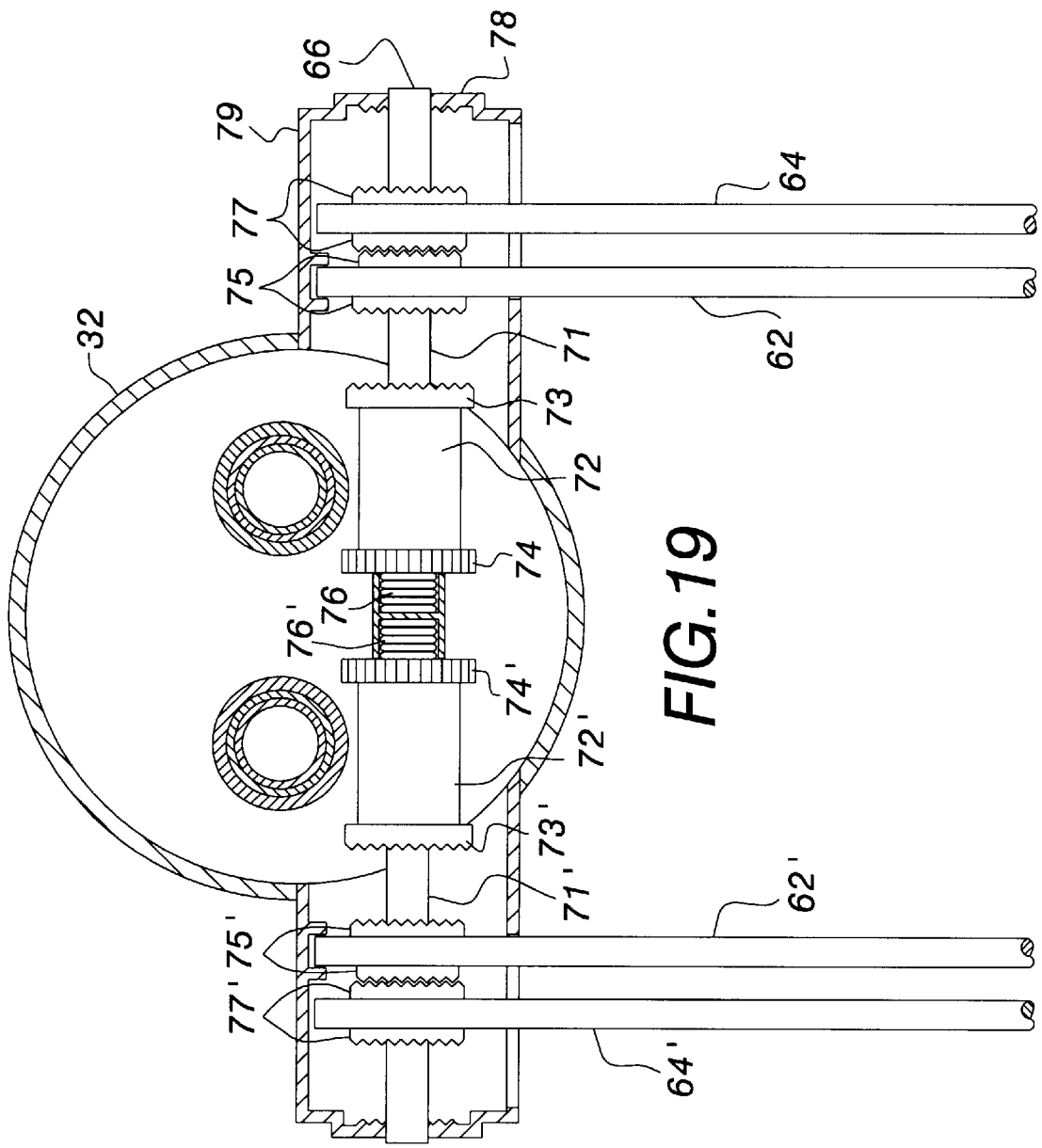
FIG. 19 is a sectional view of the proximal controls when the button is pressed.

As illustrated in FIGS. 1A, 18, and 19, proximal controls 60 of the preferred embodiment include two sets of scissor type handles 62 and 64 and 62' and 64' extending out of housing 79 disposed on barrel 32. The handles can be pivoted towards one another to cause movement of the associated pair of jaw members 50A and 50B and jaw members 50A' and 50B', respectively. The operation of one set of handles 62 and 64 is discussed in detail below with respect to driver 40. However, the other set of handlers 62' and 64' operate in connection with driver 50 in a similar manner.

Button 66 is provided proximate an axis of rotation or handles 62 and 64. Depressing button 66 disengages handles 62 and 64 from driver 40 and permits handles 62 and 64 to be rotated in concert about the axis of rotation as indicated by arrow A in FIG. 1A. This allows the surgeon to orient handles 62 and 64 in a desired manner before or during surgery. As illustrated in FIG. 18, operating member 72 is rotatably disposed on shaft 71 and has geared portion 74 that is engaged with collar 55 that is disposed on outer member 42 of driver 40. Operating member 72 is fixed axially on shaft 71 and has radially extending serrated teeth 73 formed on one side.

Handle 62 is also rotatably mounted on shaft 71, is slidable along shaft 71, and is fixed in place by projections formed on housing 79. Handle 62 has serrated teeth 75 on each side thereof at a position around shaft 71. Shaft 71 is normally biased to the right in FIG. 18 by spring 76 to press serrated teeth 73 into engagement with serrated teeth 75 thus fixing the relative position of operating member 72 and handle 62. Handle 64 is rotatably mounted on shaft 71 and fixed axially on shaft 71. Radially extending serrated teeth 77 are formed on each side of handle 64 proximate shaft 71 and serrated teeth 77 are normally biased by spring 76 into engagement with teeth formed on housing 79 to fix the position of handle 64 with respect to barrel 32. In this state handle 62 is coupled to the outer member of driver 40 and handle 64 is fixed in position. Pressing handle 62 towards handle 64 will cause outer member 42 to move distally relative to inner member 44.

When shaft 71 is moved to the left, as illustrated in FIG. 19, by pressing button 66' serrated teeth 77 engage serrated teeth 75 to fix the relation positions of handle 62 and 64 and serrated teeth 73 are disengaged from serrated teeth 75 to disengage handle 62 from driver 140. This permits the set of handles 62 and 64 to be rotated to the desired orientation without affecting needle driver 40.

Angled cam surfaces 52A and 52B are formed on outer surfaces of arms 51A and 51B respectively (see FIG. 5A), at positions near the distal end of outer member 42. When outer member 42 moves distally over cam surfaces 52A and 52B jaw members 50A and 50B are pressed toward one another to the closed position shown in FIGS. 3A, 3B, and 4A, and 4B. Therefore, compression of handles 62 and 64 closes jaw members 50A and 50B and compression of handles 62' and 64' closes jaw members 50A' and 50B'. Cam surface 52A and 52B can be formed by bent portions defined on legs 51A and 52B or by separate elements that are attached to, or formed on, legs 51A and 51B. Release of handles 62 and 64 causes jaw members 50A and 50B to return to the open position due to the resilient bias of jaw members 50A and 50B. Also, outer member 42 can be biased distally or handles 62 and 64 can be biased apart. Lock protrusions 63 and 65 are disposed on handles 62 and 64 respectively. Lock protrusions 63 and 65 are serrated to interlock and allow the position of handles 62 and 64 to be maintained in a state corresponding to a desired position of jaw members 50A and 50B. Lock protrusions 63 and 65 can be pivoted to a position at which they will not interlock if desired. Note that handles 62, 64, 62', and 64' are configured to be grasped while the surgeon's fingers pass through openings in the handles or while the surgeon's fingers are wrapped around outer portions of the handles to increase comfort and adaptability.

Needle catcher 50 is constructed similarly to needle driver 40 and thus further detailed description thereof is omitted. Also, handles 62' and 64' operate needle catcher 50 in a similar manner. It will be appreciated that the jaw members of needle driver 40 and needle catcher 50 can be of different configurations, such as those described above, dependent upon procedural use and other considerations. Also, cutting elements 53 can be provided on the jaw members as needed to cut suture material or tissue, as illustrated in FIGS. 4A and 4B.

The shafts of needle driver 40 and needle catcher 50 (which shafts are constituted of the respective inner member and the respective outer member) are disposed in channels 38b and 38d respectively to extend through barrel 32 and can be rotated about their respective longitudinal axes relative to barrel 32 by rotating knob 48 (for needle driver 40) or knob 48' (for needle catcher 50). Push buttons 49 and 49' are respectively provided for unlocking knobs 48 and 48'. When the push buttons are not depressed, the respective needle holder is locked in position. Knobs 48 and 48' can be coupled to needle driver 40 and needle catcher 50 respectively by gears as disclosed in the copending application entitled "Surgical Instrument with Multiple Rotatably Mounted Offset End Effectors and Method of Using the Same", the disclosure of which is incorporated herein by reference. Also, arms 51A and 51B of needle driver 40 extend beyond arms 51A' and 51B' of needle catcher 50, i.e. the transverse portion of the arms are in different planes, as illustrated in FIGS. 4A and 4B, to permit the arms to be placed in an overlapped crossed position (see FIGS. 3A and 3B). Further, needle driver 40 and/or needle catcher 50 can be moveable in distal and proximal directions as indicated in FIG. 1B.

Channel 38a and channel 38c can be used as operating channels for suction devices, irrigation devices, or any other appropriate instrument such as a cautery device or the like. Also, aperture 70 is formed in a position of arm 51B that is proximal a distal end of inner member 44 to define an operating channel through needle driver 40. Similarly, aperture 70' is formed in arm 51B' to define an operating channel through needle catcher 50.

In use, suturing instrument 30 is inserted into a body cavity using known techniques, while needle driver 40 and needle catcher 50 are in the insertion position, or parked position, illustrated in FIGS. 3A, 3B and 6A. Note that the entire device can be inserted through a single puncture site. Also, in this position, jaw members 50A and 50B and 50A' and 50B' as well as needle N are disposed within the diametrical dimension of barrel 32 because the respective arms are crossed over one another. By grasping proximal controls 60, the distal end of suturing instrument 30 is guided to the operative site through a portal sleeve positioned in the wall of an anatomical cavity. The portal sleeve can be positioned in the anatomical cavity wall using any suitable penetrating technique, including those creating puncture sites by means of removable obturator, such as trocars, and can include a valve housing, if desired, to prevent loss of pneumoperitoneum during insertion and withdrawal of the instrument. Further, retractable sheath 54, which is illustrated in phantom in FIG. 3A, (or any appropriate structure) can be provided to facilitate insertion through a portal sleeve valve by protecting needle driver 40 and needle catcher 50. Visualization of the endoscopic procedure can be accomplished using a conventional endoscope incorporated into channel 38a, for example (known as single puncture operation) or separately positioned within the anatomical cavity through a second portal sleeve located at another puncture site (known as double puncture operation).

Prior to insertion through a portal sleeve or the like, button 66 is pressed and handles 62 and 64 are oriented at the desired angle. Then button 66 is released and handles 62 and 64 are pressed together by the surgeon so that needle N is held tightly between jaw members 50A and 50B of needle driver 40. Lock protrusions 63 and 65 maintain handles 62 and 64 in the compressed state to permit the needle to be securely held while freeing the surgeon's hands for other manipulation. Alternatively, needle N can be introduced into the body cavity by a separate instrument through a separate puncture sight. In this embodiment, needle N is of a semi-circular configuration. However, needle N can be straight or of any other appropriate shape. Prior to suturing, needle catcher 50 is set to receive the tip of needle N by moving jaw members 50A' and 50B' to the open position. This is accomplished by permitting handles 62' and 64' to move apart due to the biasing force discussed above.

Referring to FIGS. 6A–C, which illustrate a suturing process after insertion, the shaft of needle holder apparatus 40 is rotated in a counter-clockwise direction, by rotating knob 48, as viewed in FIGS. 6A–6C to the position indicated by the dotted line in FIG. 6B and needle catcher 50 is rotated in a counter-clockwise direction, by rotating knob 48', to the position illustrated by the solid line in FIG. 6E, to permit anatomical tissue T, which is to be sutured, to be positioned between the tip of needle N and jaw members 50A' and 50B' of needle catcher 50. Subsequently, the shaft of needle driver 40 is rotated further in a counter-clockwise direction to drive needle N through a portion of the tissue while jaw members 50A' and 50B' of needle catcher 50 support the tissue from an opposite side as illustrated by the solid lines in FIG. 6B. A tip of needle N is thus caused to pass between jaw members 50A' and 50B,' of the needle catcher 50 as shown by the solid line in FIG. 6B.

With needle N positioned in needle catcher 50, handles 62' and 64' are pressed together by the surgeon to grasp needle N between jaw members 50A' and 50B'. Handles 62 and 64 are then released from the compressed position, by moving handles 62 and 64 appropriately, to place jaw members 50A and 50B in the open position and thus release needle N from needle driver 40. Subsequently, the shaft of needle driver 40 can be rotated in a clockwise direction to receive the shank of needle N once again at the position shown by the solid lines in FIG. 6C. Alternatively, the shaft of needle catcher 50 can be rotated counter-clockwise to pass the needle back to needle driver 40 at another location. Jaw members 50A' and 50B' can be opened, by operating handles 62' and 64', and jaw members 50A and 50B can be closed and the shaft of needle driver 40 can be rotated back in the counter-clockwise direction to pull needle N out of needle catcher 50 and pull suture S material that is connected to needle N through the tissue. A second stitch can be made in a manner similar to the first stitch. Alternatively, needle N can be pulled through the tissue merely by rotating the shaft of needle catcher 50 in the counter-clockwise direction. It is clear from the drawings that the movement of the needle is through an arcuate path that extends beyond the diameter of barrel 32 and is in a plane that is perpendicular to the axis of barrel 32. This provides a large working span. Also, this movement is accomplished merely by rotating knobs 48 and 48'. Note that needle N can be straight or curved. Also, suture S can be connected to any portion of needle N and can be stored in operating channel 38a with or without needle N. Further, suturing and manipulation can be accomplished by rotating barrel 32 in its entirety with the needle holders locked in position relative to barrel 132.

At any point during the operative procedure, channel 38c can be used for irrigation or aspiration, can serve as a space for holding suture material S and/or needle N or as a portal for the introduction of other medical instruments such as, forceps, cutting members, ligators, or cautery devices. Also, channels 38a and 38b can be used for irrigation, aspiration, insertion of an instrument or the like by utilizing the passage through inner member 44 of needle driver 40 and/or through inner member 44' of needle catcher 50. Proximal apertures 90–93 are provided for access to operating channels 38a–39d respectively.

In the suturing method described above, needle N is grasped further along the shank thereof in each stitch. Therefore, the number of consecutive stitches that can be made is limited by the length of needle N. A retractable plate can be provided, through one of the operating channels for example, to push the needle further into the jaws. However, this requires additional moving parts. By operating the first preferred embodiment in a slightly different manner, this limitation can be avoided. This method of suturing is illustrated in FIGS. 7A–D. In this, method suturing instrument 30 is inserted in the manner described above with arms of needle driver 40 crossing arms of the needle catcher 50, as illustrated in FIG. 7A. A first stitch is accomplished by placing the arms in the position illustrated by the solid lines in FIG. 7B in the same manner as described above with reference to FIGS. 6A–C. However, as illustrated in FIG. 7C, after needle N is pulled through the tissue by rotating the shaft of needle catcher 50 in a counterclockwise direction, the shaft of needle driver 40 is rotated clockwise eventually to place jaw members 50A and 50B on the same side of the tissue as jaw members 50A' and 50B' (See FIG. 7D), while needle catcher 50 is in the position illustrated by the solid line in FIG. 7C and the dotted line in FIG. 7D.

To replace needle N in needle driver 40, needle catcher 50 is rotated clockwise from the position illustrated by the dotted line in FIG. 7D to the position illustrated by the solid line in FIG. 7D and proximal control 60 is manipulated so that jaw members 50A and 50B are operated appropriately to grasp needle N. With needle N now grasped again by needle driver 40, at the very end of needle N, a second stitch can be made using the full length of needle N. Of course, subsequent stitches can be made in the same manner with needle N being replaced in needle driver 40 in its original position each time. Note that suture S is omitted in some drawings for clarity.

Alternatively, to replace needle N in needle driver 40, the distal end of instrument 30 can be lowered from the position illustrated in FIG. 7C, as indicated by arrow A. Subsequently, needle catcher 50 can be rotated in the clockwise direction, as indicated by arrow C, to place needle N between jaws 50A and 50B of needle driver 40. Instrument 30 is then ready for a subsequent stitch.

Needle driver 40 and needle catcher 50 can be modified to suture anatomical tissue with straight or slightly curved suture needles by shaping the jaw members appropriately to receive and hold the needle. Also, the jaw members can be rotatable on the arms to accept needle N more smoothly. Further, known knotting elements, such as knotting element 96 shown in FIG. 7D can be used in lieu of traditional knotting techniques during the suturing procedure. Some examples of suitable knotting elements for this purpose are described in pending applications Ser. No. 08/366,285, filed Dec. 29, 1994; Ser. No. 08/377,723, filed Jan. 25, 1995; Ser. No. 08/401,002, filed Mar. 9, 1995; and Ser. No. 08/585,875, filed Jan. 16, 1996, the disclosures of which are incorporated herein by reference. In addition, if both axial ends of needle N are provided with sharp, tissue penetrating tips, it is possible to penetrate the anatomical tissue at multiple locations in order to form a continuous run of stitches merely manipulating needle catcher 50 and needle driver 40 in a "shuttle" manner, i.e. passing the needle back and forth through the tissue in alternating directions. Further, needle N can be held between jaws 50A and 50B while extending along the lengthwise direction of instrument 30 during insertion. In this case needle N can be seated in grooves formed along grasping surfaces of jaw members 50A and 50B or jaw members 50A' and 50B'.

From the above, it will be appreciated that the suturing instrument according to the present invention permits suturing of anatomical tissue during endoscopic procedures without the need of having to use multiple needle holding instruments inserted through multiple puncture sites. Needle driver 40 and Needle catcher 50 each are movable and operable to grasp and release a suture needle N so that the suture needle N can be driven through anatomical tissue positioned between needle driver 40 and needle catcher 50, and can be moved to pull the suture material through the anatomical tissue with a large working span.

Operation of the preferred embodiment in combination with a ligator instrument is discussed below. Operating channels extend along the length of the suturing device through inner members 44 and 44' and outer members 42 and 42' that define a shaft of needle driver 40 and needle catcher 50 as described above. As noted above, any appropriate instrument having a desired end effector can be inserted through the operating channels to extend out of either aperture 70 or 70'.

As an example, ligator 80 can be inserted from into proximal aperture 90 at the proximal end of barrel 32 through the operating channel to extend out of aperture 70 at the distal end of needle driver 40 as shown in FIGS. 8A and in phantom in FIG. 1. FIG. 9 illustrates ligator 80 removed from barrel 32 for illustrative purposes. Ligator 80 consists of tubular member 82 having tapered portion 84 at a distal end and handle 86 at a proximal end. A length of suture material S extends through tubular member 82. One end of suture material S is fastened to handle 86. The other end of suture material S extends out of an opening formed in tapered portion 84 and is formed into loop L by slipknot 83, which can be a knotting element, formed at an end portion of suture material S and around a portion of suture material S near tapered portion 84. The opening in tapered portion 84 is large enough to permit unknotted portions of suture material S to pass therethrough but not large enough to permit slip knot 83 to pass therethrough.

Handle 86 can be separated from tubular member 82 as shown by the dotted line in FIG. 10. Since handle 86 can protrude from the proximal end of instrument 30, though proximal aperture 90, or proximal apertures 91–93, (See FIG. 1) it can be manipulated by the surgeon. In particular, handle 86 can be pulled away from tubular member 82 to pull suturing material S through slipknot 83 to thereby reduce the size of loop L. This can facilitate knotting of suture material that has been pulled through the tissue by needle catcher 40 or needle driver 50 as is described below.

During a suturing process, a shank of needle N is grasped in jaw members 50A and 50B of needle driver 40. A length of suturing material is attached to the shank of needle N and a loop is formed on a free end of the suturing material by knotting element 96 as illustrated in FIG. 8A. Needle driver 40 and needle catcher 50 are manipulated in the manner described above to pass needle N through the tissue to be sutured, such as the folded vaginal wall tissue T illustrated in FIG. 8. Needle driver 40 is then manipulated to pull needle N through loop L of suture material on the end of ligator 80 to the position illustrated in FIG. 8A (in which the tissue has been moved relative to the instrument for clarity). Ligator 80 is slidably mounted in barrel 32 and thus can be moved axially with respect to needle driver 40. This facilitates passing needle N through loop L. Also, needle driver 40 and needle catcher 50 can be movable in the distal and proximal directions as disclosed in the copending application entitled "Surgical Instrument with Multiple Rotatably Mounted Offset End Effectors and Method of Using the Same", the disclosure of which is incorporated herein by reference.

Then, needle driver 40 can be manipulated to pull suture material snugly into tissue T and seat knotting element 96 against one side of tissue T. Subsequently, loop L can be tightened around the suture material on the other side of tissue T by pulling on handle 86. This secures the suture material against the other side of tissue T so that the suture material cannot pass back through tissue T. The suture material can then be cut from needle N and ligator 80 by cutting members 53 formed in the jaws of needle driver 40, needle catcher 50, or on the end of ligator 80.

FIG. 8B illustrates an alternative ligator arrangement in which the suture material attached to the needle extends from slipnot 83 (also referred to as a knotting element). Otherwise, the structure and operation of this arrangement is the same as that of FIG. 8A.

A proximal end of ligator 80 extends out of proximal aperture 90 to permit the surgeon to manipulate handle 86 to thereby tighten loop L in the manner discussed above and as illustrated by the dotted line in FIG. 1. A plurality of ligators 80 can extend through different operating channels or a plurality of ligators 80 can be housed as a cluster in a single tubular member that extends through a single operating channel as illustrated in FIGS. 10–13. As illustrated in FIGS. 12 and 13, the plural loops of ligators 80 can all extend through a slot formed in sheath 87 that covers and end of a cluster of ligators 80. Each of the plural loops can be used to secure suture in the manner described above. FIGS. 10 and 11 illustrate a cluster of ligators 8 that are evenly dispersed throughout the cross section of a tubular member housing the ligators. FIGS. 12 and 13 illustrate a cluster of ligators 80 in which the distal end of ligators 80 are staggered to permit the loops of ligators 80 to all extend downward and to be separated from one another for sequential use. These ligators 80 can each be coupled to a suture needle by suture material in the manner described above.

The preferred embodiment disclosed above has jaw members that are biased to an open position and closed by interaction between a cam and the outer member. The modification illustrated in FIGS. 14 and 15 uses pivoting jaw members. Instrument 30 includes needle driver 40 and needle catcher 50 disposed within operating channels thereof. Needle driver 40 includes outer member 42, inner member 44 disposed in outer member 42, and jaw members 50A and 50B coupled to a distal end of inner member 44. Outer member 42 has a bent perpendicular segment disposed perpendicularly or angularly to a main body of outer member 42 and an offset distal segment extending from the angled segment and disposed Parallel to the main body of the outer member 42. Both the bent segment and the distal segment extend out of a distal end of barrel 32. A channel extends entirely through outer member 42 including the bent segment and the distal segment.

Inner member 44 includes a main body disposed in the main body of outer member 42, a bent perpendicular segment disposed in the bent segment of outer member 42 and a Y-shaped segment 145 disposed in the distal segment of outer member 42. A passage extends entirely through the main body of inner member 44 in axial or longitudinal alignment with aperture 70 formed in the angled segment of the outer member 42 such that ligator 80, or another instrument, can pass therethrough. The bent segments of inner member 44 and outer member 42 define an arm or connecting member between the shaft and offset jaws.

Y-shaped segment 145 has outwardly extending portions 147 that are pivotally connected to legs 149A and 149B extending from jaw members 50A and 50B, respectively. Legs 149A and 149B are angled inwardly from their respective jaw members to overlap one another in cross-wise fashion. Proximal ends of legs 149A and 149B are pivotally connected to extending portions 147, respectively, at pivots. These pivots also permit extending portions 147 to slide axially along legs 149A and 149B. Legs 149A and 149B are pivotally connected to one another, where they cross, by a pivot. This pivot is fixedly secured to outer member 142. Inner member 44 is slidably disposed in outer member 42 to permit longitudinal movement relative thereto.

There is adequate clearance between the bent segment of inner member 44 and the bent segment of outer member 42 to permit inner member 44 to be moved longitudinally, relative to outer member 42. When inner member 44 is moved in the proximal direction, jaw members 50A and 50B are placed in the closed position by the pivoting motion of legs 149A and 149B, as illustrated in FIG. 14. On the other hand, when inner member 44 is moved in the distal direction, jaw members 50A and 50B are placed in the open position by the pivoting motion of legs 149A and 149B, as illustrated in FIG. 15. Of course, relative movement of inner member 44 can be accomplished by proximal end controls in the manner disclosed above, or in any other appropriate manner. A slot can be formed in a distal end of outer member 42 to permit ends of legs 149A and 149B to extend out of outer member 42, in a radial direction thereof, when jaw members 50A and 50B are in the open position, if necessary. This permits a greater stroke of jaw members 50A and 50B. The jaws of needle catcher 50 can operate in a similar manner and like parts of needle catcher 50 are labeled with like reference numerals with the added suffix "'".

A suturing instrument according to a second preferred embodiment is illustrated at 130 in FIGS. 16 and 17 and 21A and 21B. The second preferred embodiment includes needle driver 140 and needle catcher 150 and is similar to the first preferred embodiment except for the configuration of arms 151A and 151B, 151A' and 151B'. Specifically, for needle driver 140, arms 151A and 151B are curved to correspond substantially with the curvature of the circumferential outer surface of barrel 32. Jaw members 150A and 150B are moveably mounted on a distal end of arms 151A and 151B respectively to open and close in a manner similar to the embodiments disclosed above. Jaw members 150A and 150B can be operated in a manner similar to the jaw members of the first preferred embodiment, for example. Once again, like parts of needle catcher are distinguished by the suffix "'".

Figure 16:
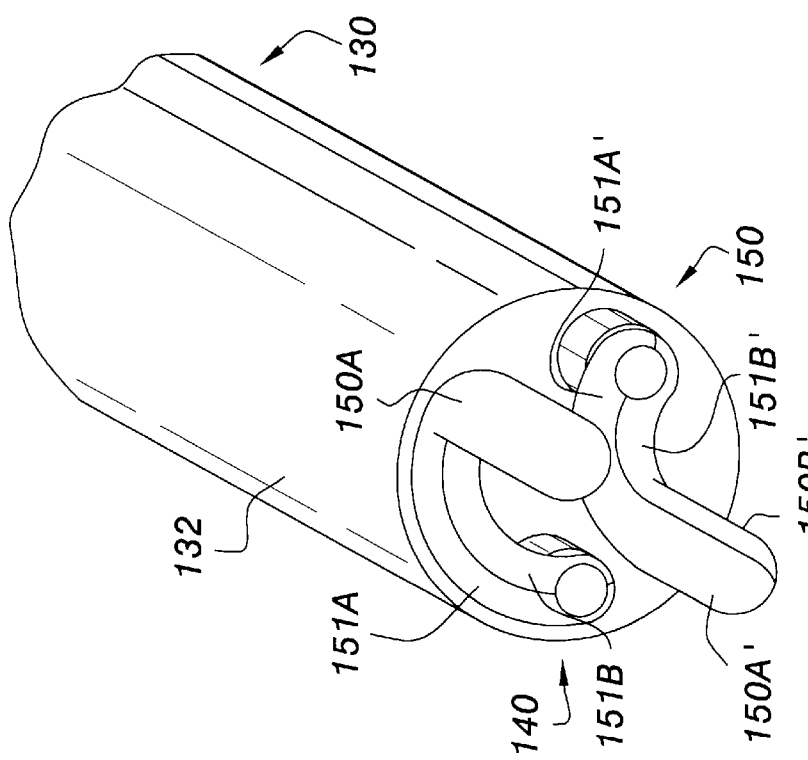
FIG. 16 is a perspective view of a distal end of a second preferred embodiment in the insertion position.

As is best illustrated in FIG. 16, arms 151A, 151B, 151A' and 151B' can easily be confined within the diametrical dimension of barrel 32 during insertion. During suturing, or other procedures, the arms can be moved, by rotating this corresponding shafts to cause jaw members 150A and 150B and 150A' and 150B' to be moved through a path that is outside of the diametrical dimension of barrel 32 as illustrated in FIG. 17. This embodiment can be used to suture tissue in a manner similar to the first embodiment. However, the insertion position of this embodiment, in which the arms and jaw members are contained within the diametrical dimension of barrel 132 (see FIG. 16) does not require that the arms cross one another. Therefore, the arms need not be disposed in different planes, but can be movable in the distal and proximal directions if desired. In operation, a needle may be grasped by the jaw members and passed through tissue in a manner similar to the embodiments discussed above. Also, the jaw members and shafts of this embodiment can be manipulated in the same way as the first embodiment.

FIG. 20 illustrates an alternative needle driver 40 in which arm member 51A is coupled to inner member 44 and arm member 51B is coupled to outer member 42. Relative rotation between inner member 42 and outer member 44 causes jaws 50A and 50B to open/close. Rotation in concert causes a needle grasped by jaws 50A and 50B to be moved. Also, longitudinal and transverse grooves are formed in the jaws to facilitate grasping a needle.

While the needle driver and the needle catcher have been described herein as being independently controlled by separate operating mechanisms, such as push buttons slidably disposed along slots formed in the instrument housing, it will be appreciated that a single operating mechanism can be used to synchronize movement of the needle driver and the needle catcher relative to one another as well as operation of their respective needle holding members to further simplify the suturing process by allowing one-hand operation of the instrument. For example, a single operating mechanism utilizing conventional gearing and cam arrangements can enable the user to rotate the needle catcher toward a suture needle held by the needle driver in a first direction along an arcuate path in response to a single squeeze of a handle or trigger while also causing the jaws of the needle driver to open and the jaws of the needle catcher to close so that the suture needle is transferred or passed to the needle catcher. The user can then release the handle or trigger to cause the needle catcher to rotate away from the needle driver in a second, opposite direction along the arcuate path thereby pulling the suture needle through anatomical tissue. If desired, such an operating mechanism can move the needle driver toward the needle catcher when the handle is squeezed and also move the needle driver away from the needle catcher when the handle is released. Once the needle has been pulled through the tissue, the operating mechanism can reverse the process so that, for example, if the handle is squeezed again, the operating system will cause the needle catcher to rotate toward the needle driver in the first direction along the arcuate path while also causing the jaws of the needle catcher to open and the jaws of the needle driver to close, thereby transferring the suture needle back to the needle driver for continued suturing.

In particular, handles 62 and 64 can be coupled to both needle driver 40 and needle catcher 50 in a manner which causes the desired rotation of the shafts of needle driver 40 and needle catcher 50 and the opening and closing operation of the respective jaws necessary for a single stitch, or multiple stitches, to be effected merely by squeezing and releasing handles 62 and 64 once or multiple times. The mechanism coupling handles 62 and 64 to needle driver 40 and needle catcher 50 can be designed to accomplish any of the stitching functions disclosed above or any other appropriate motion. Such an automatic mechanism facilitates suturing by minimizing fatigue on the surgeon and reducing the possibility of operational errors.

One example of an automatic mechanism for effecting one-handed operation of suturing instrument 30 is illustrated in FIGS. 21–24. Handle 64 is fixedly connected to housing 79. Handle 62 is movable and extends through a slot in housing 79 to be mounted on shaft 120 to cause shaft 120 to rotate when handle 62 is pivoted towards handle 54. Beveled gears 122 and 124 are also mounted on shaft 120 to rotate with shaft 120. Biasing member 126, shown as a coiled spring, biases handle 52 away from handle 64 to the illustrated position.

Beveled gears 122 and 124 are coupled respectively to beveled gears 126 and 128 that are fixed on outer member 42 and outer member 42' respectively. Beveled gear 124 is coupled directly to beveled gear 126 and beveled gear 122 is coupled to beveled gear 128 through beveled gear 130. Accordingly, rotation of shaft 120 causes outer member 42 to rotate in a first direction and causes outer member 42' to rotate in a second direction opposite to the first direction. The corresponding inner members are configured to rotate with the outer members.

Projection 132 extends from inner member 44' through slots formed in outer member 42' and beveled gear 128, as is best illustrated in FIGS. 22–24. A free end of projection 132 slides in cam groove 136 formed in cylindrical member 170. Similarly, projection 134 extends from inner member 44 and slides in cam groove 138 formed in cylindrical member 172. The cam grooves are shaped to cause the respective inner members to move axially, in distal and proximal directions, after the inner members rotate through a predetermined angle.

In operation, a needle is grasped in jaws of needle driver 40 in the illustrated position. When the surgeon squeezes handle 62 towards handle 64, shaft 120 rotates to cause needle driver 40 to rotate in a clockwise direction, as viewed from the distal end, and to cause needle catcher 50 to rotate in a counterclockwise direction, as viewed from the distal end. This results in the needle being pushed through tissue and into the jaws of needle holder 50 at which time cam grooves 136 and 138 cause the inner members to move relative to the outer members in a manner to open jaws of needle driver 40 and close jaws of needle catcher 50. Releasing handles 62 and 64 permits needle holder 40 and needle catcher 50 to rotate in opposite directions due to the force of biasing member 126 as projections 132 and 134 continue in the same direction through cam grooves 136 and 138. Now the instrument can be compressed again to transfer the needle back to needle driver 40 for another stitch.

In some of the embodiments discussed above, two opposed jaw members are moveable toward one another. However, one of the jaw members can be fixed and the other jaw member can be moveable. Also, any appropriate proximal controls can be used to accomplish the disclosed movement. For example, any of the proximal controls disclosed in applicant's copending application entitled "Surgical Instrument With Multiple Rotatably Mounted Offset End Effectors and Method of Using the Same", the disclosure of which is incorporated herein by reference, can be used.

The needle driver and the needle catcher, i.e. the needle holders, can be of the same design or of different designs as long as at least one is capable of grasping and releasing a needle. Also, the needle holders can be disposed in various portions of the barrel. For example, instrument 30 can have any of the configurations disclosed in the copending application entitled "Surgical Instrument With Multiple Rotatably Mounted Offset End Effectors and Method of Using the Same", the disclosure of which is incorporated herein by reference. The jaw members can be configured to hold any type of needle including, but not limited to, straight and curved needles. Further, the function of the needle driver and the needle catcher can be interchanged and suturing can be accomplished in the opposite direction depending on whether the surgeon is right-handed or left-handed.

One or more lengths of suture material can be attached to each suture needle at any desirable location along the body or tip of the needle including, but not limited to, the proximal end of the needle, intermediate or medial portions of the needle body, or locations adjacent the tip of the needle. It will also be appreciated that the suturing instrument according to the present invention can be used with any type of standard suturing needle including, but not limited to, needles having sharp or blunt tissue penetrating tips, and needles having tissue penetrating tips at opposite axial ends of a needle body. The arms, or connecting member, can extend transversely or of any angle with respect to the shafts.

The holding mechanisms of the needle catcher and the needle driver shown and described herein are merely exemplary of the types of needle holding mechanisms that can be used according to the present invention. Accordingly, the jaw members and other components can have any suitable configuration for cooperatively grasping needles to suture anatomical tissue including, but not limited to, configurations wherein the jaw members pivot, slide or otherwise move relative to one another to capture and release a needle. The jaw members can, for example, be of straight, curved or angled configuration and can be provided with ribs, grooves, slots and/or holes along grasping surfaces to assure a positive grip. The jaw members can also carry cutting members, such as slots with sharp edges or protruding blades, and can have opposed arcuate or concave portions for clamping tubular objects, such as organs, without compressing the objects. Also, only one, or more than two needle holding devices can be provided in the suturing device as needed. Further, the jaws can be configured to carry a needle in a longitudinal manner during insertion of the device and the needle can be turned transversely for suturing.

Also, the "needle catcher" can be a device without jaws for merely supporting tissue during suturing. In such a case the needle driver pushes the needle through tissue while the tissue is supported at a back surface by the "needle catcher". Further, one of the needle catcher and needle driver can be fixed.

The mechanisms for moving the needle catcher and needle driver relative to one another are merely exemplary of the types of mechanisms that can be used to perform these functions and other mechanisms can be used. The particular length and curvature of the suture needles shown and described herein as well as any angular displacements of the needle driver and catcher shown and described herein are merely exemplary, and it will be appreciated that other needle lengths and angular displacements can be used. For example, the needle holders can be flexible and can be drawn into the barrel proximally to be placed in an insertion position.

One of the needle holders can be used as forceps, to grasp the tissue, during suturing or can contain a clip applicator. Therefore, the invention can be used for pickup and cutting, pickup and clipping, pickup and suturing, or lysis of adhesion procedures. Alternatively, a forceps device can be inserted through the operating channel formed in the shaft of one of the needle holders or another operating channel. The jaw members can be used as unipolar or bipolar cautery electrodes by being coupled to an electrical power source by connector 110. Also, a button can be provided to switch the electric power from one set of jaws to the other, button 66 for example. Further, tissue can be clamped between adjacent needle holders or tissue can be retracted by placing adjacent needle holders between tissue portions and moving the needle holders apart.

The components of the suturing instrument of the present invention can be made of any suitable, medical grade materials to permit sterilization for reuse or disposal for single patient use. The components can be made of multiple parts of various configurations and materials to reduce cost. The invention can have various valves, stop-cocks and seals therein to control the flow of fluid and medical devices through the suturing instrument.

In as much as the present invention is subject to many variations, modifications and changes in detail, it is intended that all subject matter discussed above or shown in the accompanying drawings be interpreted as illustrative only and not be construed as limiting the scope of the invention which is defined by the appended claims.

What is claimed is:

1. A suturing instrument for causing a needle to pass through anatomical tissue, comprising:

an elongated barrel extending along a centrally-disposed longitudinal axis and having a distal end and a proximal end;

a handle coupled to said proximal end of said barrel;

a needle driver assembly comprising:

a driver shaft extending longitudinally through at least a portion of said barrel and disposed offset relative to the centrally-disposed longitudinal axis;

a driver connecting member coupled to a driver shaft end of said driver shaft projecting from said barrel, the driver connecting member extending transversely relative to the centrally-disposed longitudinal axis; and driver needle holding members coupled to and extending longitudinally from said driver connecting member, the driver needle holding members being parallel to the centrally-disposed longitudinal axis when in a closed state, said driver needle holding members having a longitudinal axis that is offset from a longitudinal axis of said driver shaft; and a needle catcher assembly comprising:

a catcher shaft extending longitudinally through at least a portion of said barrel and disposed offset relative to the centrally-disposed longitudinal axis;

a catcher connecting member coupled to a catcher shaft end of said catcher shaft projecting from said barrel, the catcher connecting member extending transversely relative to the centrally-disposed longitudinal axis; and a support member coupled to and extending longitudinally from said catcher connecting member;

wherein said driver connecting member is rotatably mounted in said barrel to rotate about an axis parallel to the centrally-located longitudinal axis of said barrel to move said driver connecting member between a first position, in which said driver needle holding members are contained entirely within a diametrical dimension of said barrel, and a second position, in which at least a portion of said driver needle holding members extend beyond the diametrical dimension of said barrel.

2. An instrument as recited in claim 1, wherein said catcher connecting member is rotatably coupled to said barrel to move said catcher connecting member between a first position, in which said support member is contained entirely within the diametrical dimension of said barrel, and a second position, in which at least a portion of said support member extends beyond the diametrical dimension of said barrel.

3. An instrument as recited in claim 2, wherein said support member comprises needle holding members.

4. An instrument as recited in claim 2, wherein said driver connecting member is mounted on a driver shaft extending through at least a portion of said barrel and said catcher connecting member is mounted on a catcher shaft extending through at least a portion of said barrel, said driver shaft and said catcher shaft are mounted in said barrel to rotate about axes that are substantially parallel to the longitudinal axis of said barrel.

5. An instrument as recited in claim 4, wherein said support member comprises catcher needle holding members.

6. An instrument as recited in claim 5 wherein said driver connecting member is a driver arm that extends from a distal end of said driver shaft in a direction substantially perpendicular to an axis of rotation of said driver shaft and said catcher connecting member is a catcher arm that extends from a distal end of said catcher shaft in a direction substantially perpendicular to an axis of rotation of said catcher shaft.

7. An instrument as recited in claim 6 wherein said driver arm comprises a pair of driver arm member and said catcher arm comprises a pair of catcher arm members.

8. An instrument as recited in claim 7, further comprising:

a driver opening device for moving said driver needle holding members toward and away from one another; and a catcher opening device for moving said catcher needle holding members toward and away from one another.

9. An instrument as recited in claim 8, wherein said catcher arm is in a plane which is different than that of said driver arm.

10. An instrument as recited in claim 4, further comprising:

a driver operating channel defined in said driver shaft and extending from said proximal end to said distal end.

11. An instrument as recited in claim 4, further comprising a catcher operating channel defined in said catcher shaft and extending from said proximal end to said distal end.

12. An instrument as recited in claim 9, further comprising:

a driver operating channel defined in said driver shaft and extending from said proximal end to said distal end.

13. An instrument as recited in claim 9, further comprising a catcher operating channel defined in said catcher shaft and extending from said proximal end to said distal end.

14. An instrument as recited in claim 10, further comprising a ligator for tightening a suture loop around a piece of suture material, said ligator being disposed in said driver operating channel.

15. An instrument as recited in claim 11 further comprising a ligator for tightening a suture loop around a piece of suture material, said ligator being disposed in said catcher operating channel.

16. An apparatus as recited in claim 12, further comprising a ligator for tightening a suture loop around a piece of suture material, said ligator being disposed in said driver operating channel.

17. An instrument as recited in claim 13, further comprising a ligator for tightening a suture loop around a piece of suture material, said ligator being disposed in said catcher operating channel.

18. An instrument as recited in claim 5 wherein said driver connecting member is an arcuate driver arm.

19. An instrument as recited in claim 5 wherein said catcher connecting member is an arcuate catcher arm.

20. An instrument as recited in claim 1, wherein a longitudinal axis of said driver needle holding members is parallel to the longitudinal axis of said barrel and a longitudinal axis of said support member is parallel to the longitudinal axis of said barrel.

21. A suturing instrument for causing a needle to pass through anatomical tissue comprising:

an elongated barrel extending along a centrally-disposed longitudinal axis and having a distal end and a proximal end;

a handle coupled to said proximal end of said barrel;

a needle driver assembly comprising:

a driver shaft extending longitudinally through at least a portion of said barrel and disposed offset relative to the centrally-disposed longitudinal axis;

a driver connecting member coupled to a driver shaft end of said driver shaft projecting from said barrel, the driver connecting member extending transversely relative to the centrally-disposed longitudinal axis; and driver needle holding members extending longitudinally from said driver connecting member, the driver needle holding members being parallel to the centrally-disposed longitudinal axis when in a closed state; and a needle catcher assembly comprising:

a catcher shaft extending longitudinally through at least a portion of said barrel and disposed offset relative to the centrally-disposed longitudinal axis;

a catcher connecting member coupled to a catcher shaft end of said catcher shaft projecting from said barrel, the catcher connecting member extending transversely relative to the centrally-disposed longitudinal axis; and a support member coupled to and extending longitudinally from said catcher connecting member;

wherein said driver connecting member is rotatably mounted in said barrel to rotate about an axis parallel to the centrally-located longitudinal axis of said barrel to move said driver connecting member between a first position, in which said driver needle holding members are contained entirely within a diametrical dimension of said barrel, and a second position, in which at least a portion of said driver needle holding members extend beyond the diametrical dimension of said barrel.

22. An instrument as recited in claim 21, wherein said catcher connecting member is rotatably coupled to said barrel to move said catcher arm between a first position, in which said support member is contained entirely within the diametrical dimension of said barrel, and a second position, in which at least a portion of said support member extends beyond the diametrical dimension of said barrel.

23. An instrument as recited in claim 22, wherein said support member comprises catcher needle holding members.

24. An instrument as recited in claim 22, wherein said driver connecting member is disposed on a driver shaft extending at least partially through said barrel and said catcher connecting member is disposed on a catcher shaft extending at least partially through said barrel, and said driver shaft and said catcher shaft are mounted in said barrel to rotate about axes that are substantially parallel to the longitudinal axis of said barrel.

25. An instrument as recited in claim 24, further comprising:

a driver opening device for moving said driver needle holdings members toward and away from one another; and a catcher opening device for moving said catcher needle holding members toward and away from one another.

26. An instrument as recited in claim 25, wherein said catcher connecting member is in a plane which is different than that of said driver connecting member.

27. An instrument as recited in claim 24, further comprising a driver operating channel defined in said driver shaft and extending from said proximal end to said distal end.

28. An instrument as recited in claim 24, further comprising a catcher operating channel defined in said catcher shaft and extending from said proximal end to said distal end.

29. An instrument as recited in claim 26, further comprising a driver operating channel defined in said driver shaft and extending from said proximal end to said distal end.

30. An instrument as recited in claim 26, further comprising a catcher operating channel defined in said catcher shaft and extending from said proximal end to said distal end.

31. An instrument as recited in claim 27, further comprising a ligator for tightening a suture loop around a piece of suture material, said ligator being disposed in said driver operating channel.

32. An instrument as recited in claim 28, further comprising a ligator for tightening a suture loop around a piece of suture material, said ligator being disposed in said catcher operating channel.

33. An apparatus as recited in claim 29, further comprising a ligator for tightening a suture loop around a piece of suture material, said ligator being disposed in said driver operating channel.

34. An instrument as recited in claim 30, further comprising a ligator for tightening a suture loop around a piece of suture material, said ligator being disposed in said catcher operating channel.

35. A method of suturing anatomical tissue using a length of suture material attached to a needle, said method comprising the steps of:

introducing a distal end of a barrel into an area proximate the anatomical tissue, the barrel extending along a longitudinal axis;

grasping the needle with driver needle holding members disposed on a driver connecting member coupled to a distal end of a driver shaft projecting from the barrel and extending transversely to the longitudinal axis the driver needle holding members having a longitudinal axis that is offset from and parallel to the longitudinal axis of the barrel and being operable by a handle coupled to a proximal end of the barrel; and rotating the driver shaft about an axis parallel with the longitudinal axis of the barrel in a first direction to cause the needle to move in an arcuate path and to cause a tip of the needle to penetrate the anatomical tissue.

36. A method as recited in claim 35, wherein said rotating step comprises rotating the barrel.

37. A method as recited in claim 35 further comprising the steps of:

grasping the needle with catcher needle holding members disposed on a catcher connecting member coupled to a distal end of the barrel, the catcher needle holding members having a longitudinal axis that is offset from a longitudinal axis of the barrel and being operable by the handle;

releasing the needle from the driver needle holding members; and rotating the catcher connecting member in the first direction about an axis parallel to the longitudinal axis of the barrel to cause the needle to move in an arcuate path and to pull the needle entirely through the anatomical tissue.

38. A method as recited in claim 35, further comprising the steps of:

inserting a ligator having a loop through an operating channel defined in the instrument; and passing the needle through the loop.

39. A method as recited in claim 38, wherein the suture material attached to the needle extends from a knotting element defining the loop.

40. A method as recited in claim 37, wherein the catcher connecting member and the driver connecting member lie in different planes.

41. A method as recited in claim 40, further comprising the steps of:

after releasing the suture needle from the driver needle holding members, rotating the driver connecting member in a second direction that is opposite to the first direction to receive a shank of the needle in the driver needle holding members;

grasping the needle in the driver needle holding members again;

releasing the needle from the catcher needle holding members; and repeating the previous steps until suturing is finished.

42. A method as recited in claim 40, further comprising the steps of:

rotating the catcher connecting member in the first direction further until the catcher needle holding members are outside of the path of the driver needle holding members;

rotating the driver connecting member in the second direction until the driver needle holding members pass beyond the catcher jaws;

rotating the catcher connecting member in the second direction until a shank of the needle is received in the driver needle holding members;

grasping the needle with the driver needle holding members;

releasing the needle from the catcher needle holding members;

rotating the catcher connecting member in the first direction until the catcher needle holding members are out of the path of the driver needle holding members; and repeating the previous steps until suturing is finished.

43. A method as recited in claim 40 wherein, during said introducing step, the driver connecting member crosses the catcher connecting member and the driver needle holding members and the catcher needle holding members are contained entirely within a diametrical dimension of said barrel.

44. A method as recited in claim 37, further comprising the steps of:

moving the barrel in an axial direction; and rotating the catcher connecting member in a second direction to cause the needle to penetrate the anatomical tissue again.

45. A method as recited in claim 37, further comprising the steps of:

moving the barrel away from the tissue; and rotating the catcher connecting member in a second direction to place the needle between the driver needle holding members.

46. A method of suturing anatomical tissue using a length of suture material attached to a needle, said method comprising the steps of:

introducing an instrument having a barrel extending along a longitudinal axis into an area proximate the anatomical tissue;

grasping the needle with a needle driver, said needle driver comprising a driver shaft extending longitudinally and projecting from the barrel, a grasping portion extending longitudinally and a driver connecting member extending transversely to the longitudinal axis and interconnecting said drive shaft and said drive needle grasping portion;

positioning the anatomical tissue between a tip of the suture needle and a needle catcher, the needle catcher comprising a catcher shaft extending longitudinally and projecting from the barrel, a catcher needle grasping portion extending longitudinally and a catcher connecting member extending transversely to the longitudinal axis and interconnecting said catcher shaft and said catcher needle grasping portion; and rotating the driver shaft in a first direction to cause the needle to move in an arcuate path and to cause a tip of the needle to penetrate the anatomical tissue.

47. A method as recited in claim 46 wherein said step of rotating the driver shaft comprises rotating said barrel.

48. A method as recited in claim 47 further comprises the steps of:

grasping the needle with the catcher grasping portion;

releasing the needle from the driver grasping portion; and rotating the catcher shaft in the first direction to cause the needle to move in an arcuate path and to pull the needle entirely through the anatomical tissue.

49. A method as recited in claim 48 wherein said step of rotating the catcher shaft comprises rotating said barrel.

50. A method of suturing anatomical tissue using a length of suture material attached to a needle, said method comprising the steps of:

introducing an instrument having a barrel extending along a longitudinal axis into an area proximate the anatomical tissue;

grasping the needle with a needle drive, said needle driver comprising a drive shaft extending longitudinally and projecting from the barrel, a needle grasping portion extending longitudinally and a driver connecting member extending transversely to the longitudinal axis and interconnecting said drive shaft and said driver needle grasping portion;

positioning the anatomical tissue between a tip of the suture needle and a needle catcher, the needle catcher comprising a catcher shaft extending longitudinally and projecting from the barrel, a catcher needle grasping portion extending longitudinally and a catcher connecting member extending transversely to the longitudinal axis and interconnecting said catcher shaft and said catcher needle grasping portion;

rotating the drive shaft in a first direction to cause the needle to move in an arcuate path and to cause a tip of the needle to penetrate the anatomical tissue; and rotating the catcher shaft in a second direction to cause a portion of the needle to be received in the catcher needle grasping portion.

51. A method as recited in claim 50 wherein said step of rotating the drive shaft and said step of rotating the catcher shaft are conducted simultaneously.

52. A method as recited in claim 50 wherein said step of rotating the drive shaft and said step of rotating the catcher shaft are conducted in seriatim.

* * * * *